(12) United States Patent
Foxlin et al.

(10) Patent No.: US 11,382,536 B2
(45) Date of Patent: Jul. 12, 2022

(54) USER IDENTIFICATION BY BIOMETRIC MONITORING DEVICE

(71) Applicant: Fitbit, Inc., San Francisco, CA (US)

(72) Inventors: Eric Foxlin, Lexington, MA (US); Molly Glauberman, San Francisco, CA (US); Erick Fuentes, Cambridge, MA (US)

(73) Assignee: Fitbit, Inc., San Francisco, CA (US)

( * ) Notice: Subject to any disclaimer, the term of this patent is extended or adjusted under 35 U.S.C. 154(b) by 0 days.

(21) Appl. No.: 16/948,390

(22) Filed: Sep. 16, 2020

(65) Prior Publication Data
US 2021/0100483 A1 Apr. 8, 2021

Related U.S. Application Data

(63) Continuation of application No. 16/829,658, filed on Mar. 25, 2020, now Pat. No. 10,806,379, which is a (Continued)

(51) Int. Cl.
*A61B 5/1171* (2016.01)
*A61B 5/00* (2006.01)
(Continued)

(52) U.S. Cl.
CPC .......... *A61B 5/1171* (2016.02); *A61B 5/0531* (2013.01); *A61B 5/117* (2013.01);
(Continued)

(58) Field of Classification Search
CPC ..... A61B 5/1171; A61B 5/0531; A61B 5/117; A61B 5/6829; G01G 19/50; H04L 67/306; H04L 67/12; G06K 9/00892; G06F 3/048
See application file for complete search history.

(56) References Cited

U.S. PATENT DOCUMENTS

| 6,583,369 | B2 | 6/2003 | Montagnino et al. |
| 6,695,207 | B1 | 2/2004 | Norris, Jr. |

(Continued)

FOREIGN PATENT DOCUMENTS

| EP | 1 721 237 | 8/2012 |
| WO | WO 12/170586 | 12/2012 |

(Continued)

OTHER PUBLICATIONS

US Office Action, dated Nov. 18, 2016, issued in U.S. Appl. No. 15/231,620.

(Continued)

*Primary Examiner* — Garrett K Atkinson
(74) *Attorney, Agent, or Firm* — Dority & Manning, P.A.

(57) ABSTRACT

Techniques for user identification by a biometric monitoring device are disclosed. In one aspect, a method of operating a biometric monitoring device may involve measuring a weight of a user in response to detecting that the user is standing on a platform, determining, based on sensor data generated by a sensor, a user parameter indicative of the user's identification, identifying one of a plurality of user profiles as corresponding to the user based on a comparison of the user parameter to parameter values and a comparison of the measured weight of the user to weight values, and updating the identified user profile based on at least one of the measured weight and the user parameter.

16 Claims, 12 Drawing Sheets

Related U.S. Application Data continuation of application No. 15/486,208, filed on Apr. 12, 2017, now Pat. No. 10,624,561.

(51) Int. Cl.
  *G01G 19/50* (2006.01)
  *H04L 67/306* (2022.01)
  *A61B 5/0531* (2021.01)
  *A61B 5/117* (2016.01)
  *G06V 40/70* (2022.01)
  *G06F 3/048* (2013.01)
  *H04L 67/12* (2022.01)

(52) U.S. Cl.
  CPC ........... *A61B 5/6829* (2013.01); *G01G 19/50* (2013.01); *G06V 40/70* (2022.01); *H04L 67/306* (2013.01); *G06F 3/048* (2013.01); *H04L 67/12* (2013.01)

(56) References Cited

U.S. PATENT DOCUMENTS

| | | | |
|---|---|---|---|
| 8,008,996 B2 | 8/2011 | Chen et al. | |
| 8,447,704 B2 | 5/2013 | Tan et al. | |
| 8,475,367 B1* | 7/2013 | Yuen | A61B 5/02007 600/300 |
| 8,684,900 B2 | 4/2014 | Tran | |
| 8,696,569 B2* | 4/2014 | Yuen | A61B 5/7275 600/300 |
| 8,747,312 B2* | 6/2014 | Yuen | A61B 5/7275 600/300 |
| 8,764,651 B2 | 7/2014 | Tran | |
| 8,922,342 B1 | 12/2014 | Ashenfelter et al. | |
| 8,983,637 B2 | 3/2015 | Glode et al. | |
| 9,084,536 B2* | 7/2015 | Yuen | A61B 5/1118 |
| 9,084,537 B2* | 7/2015 | Yuen | A61B 5/0059 |
| 9,084,538 B2* | 7/2015 | Yuen | A61B 5/4872 |
| 9,157,787 B2* | 10/2015 | Sharma | G01G 19/44 |
| 9,159,213 B1 | 10/2015 | Chun et al. | |
| 9,173,576 B2* | 11/2015 | Yuen | A61B 5/02007 |
| 9,173,577 B2* | 11/2015 | Yuen | G06F 3/0412 |
| 9,247,884 B2* | 2/2016 | Yuen | G01G 19/50 |
| 9,549,680 B2* | 1/2017 | Giovangrandi | G01G 19/50 |
| 9,667,353 B2 | 5/2017 | Å.strand et al. | |
| 9,693,711 B2 | 7/2017 | Yuen et al. | |
| 9,750,435 B2 | 9/2017 | Jun | |
| 9,782,075 B2 | 10/2017 | Redei | |
| 9,851,808 B2 | 12/2017 | Yuen et al. | |
| 10,126,830 B2 | 11/2018 | Yuen et al. | |
| 10,181,021 B2 | 1/2019 | Venkatraman et al. | |
| 10,503,268 B2 | 12/2019 | Yuen et al. | |
| 10,624,561 B2 | 4/2020 | Venkatraman et al. | |
| 10,806,379 B2 | 10/2020 | Foxlin et al. | |
| 10,942,579 B2 | 3/2021 | Yuen et al. | |
| 2002/0138768 A1 | 9/2002 | Murakami et al. | |
| 2002/0184159 A1 | 12/2002 | Tadayon et al. | |
| 2003/0061172 A1 | 3/2003 | Robinson | |
| 2003/0190062 A1 | 10/2003 | Noro et al. | |
| 2004/0230105 A1 | 11/2004 | Geva et al. | |
| 2005/0281439 A1 | 12/2005 | Lange | |
| 2006/0025282 A1 | 2/2006 | Redmann | |
| 2006/0047970 A1 | 3/2006 | Mochizuki | |
| 2006/0080525 A1 | 4/2006 | Ritter et al. | |
| 2006/0133652 A1 | 6/2006 | Iwasaki | |
| 2006/0136744 A1 | 6/2006 | Lange | |
| 2006/0224074 A1 | 10/2006 | Ouchi et al. | |
| 2006/0284639 A1 | 12/2006 | Reynolds | |
| 2007/0002141 A1 | 1/2007 | Lipton et al. | |
| 2007/0142715 A1 | 6/2007 | Banet et al. | |
| 2007/0142868 A1 | 6/2007 | Moon et al. | |
| 2007/0177770 A1 | 8/2007 | Derchak et al. | |
| 2007/0260511 A1 | 11/2007 | Bender, II et al. | |
| 2007/0263907 A1 | 11/2007 | McMakin et al. | |
| 2007/0293781 A1 | 12/2007 | Sims et al. | |
| 2008/0001735 A1 | 1/2008 | Tran | |
| 2008/0235144 A1 | 9/2008 | Phillips | |
| 2008/0287751 A1 | 11/2008 | Stivoric et al. | |
| 2008/0294019 A1 | 11/2008 | Tran | |
| 2009/0203972 A1 | 8/2009 | Heneghan et al. | |
| 2009/0232362 A1 | 9/2009 | Otsubo et al. | |
| 2009/0239709 A1 | 9/2009 | Wu | |
| 2009/0241174 A1 | 9/2009 | Rajan et al. | |
| 2009/0319221 A1 | 12/2009 | Kahn et al. | |
| 2010/0113950 A1 | 5/2010 | Lin et al. | |
| 2010/0203967 A1 | 8/2010 | Chiu et al. | |
| 2010/0207721 A1 | 8/2010 | Nakajima et al. | |
| 2010/0331145 A1 | 12/2010 | Lakovic et al. | |
| 2010/0331903 A1 | 12/2010 | Zhang et al. | |
| 2011/0004072 A1 | 1/2011 | Fletcher et al. | |
| 2011/0032105 A1 | 2/2011 | Hoffman et al. | |
| 2011/0032139 A1 | 2/2011 | Benitez et al. | |
| 2011/0152637 A1 | 6/2011 | Kateraas et al. | |
| 2011/0257554 A1 | 10/2011 | Banet et al. | |
| 2012/0007713 A1 | 1/2012 | Nasiri et al. | |
| 2012/0068820 A1 | 3/2012 | Mollicone et al. | |
| 2012/0083705 A1 | 4/2012 | Yuen et al. | |
| 2012/0115682 A1 | 5/2012 | Homsi | |
| 2012/0179636 A1 | 7/2012 | Galiana et al. | |
| 2012/0274508 A1 | 11/2012 | Brown et al. | |
| 2012/0296455 A1 | 11/2012 | Ohnemus et al. | |
| 2012/0316455 A1 | 12/2012 | Rahman et al. | |
| 2013/0030320 A1 | 1/2013 | Maier | |
| 2013/0041856 A1 | 2/2013 | Benitez et al. | |
| 2013/0106684 A1 | 5/2013 | Weast et al. | |
| 2013/0158364 A1* | 6/2013 | Hayn | A61B 5/0004 600/301 |
| 2013/0158686 A1 | 6/2013 | Zhang et al. | |
| 2013/0166048 A1 | 6/2013 | Werner et al. | |
| 2013/0204410 A1 | 8/2013 | Napolitano | |
| 2013/0227678 A1 | 8/2013 | Kang et al. | |
| 2013/0268236 A1 | 10/2013 | Yuen et al. | |
| 2013/0281805 A1 | 10/2013 | Mason et al. | |
| 2014/0059066 A1 | 2/2014 | Koloskov | |
| 2014/0067494 A1 | 3/2014 | Squires | |
| 2014/0083779 A1* | 3/2014 | Sharma | G01G 19/44 177/1 |
| 2014/0085050 A1 | 3/2014 | Luna | |
| 2014/0089672 A1 | 3/2014 | Luna et al. | |
| 2014/0099614 A1 | 4/2014 | Hu et al. | |
| 2014/0157209 A1 | 6/2014 | Dalal et al. | |
| 2014/0164611 A1 | 6/2014 | Molettiere et al. | |
| 2014/0165185 A1 | 6/2014 | Lange | |
| 2014/0180022 A1 | 6/2014 | Stivoric et al. | |
| 2014/0266860 A1 | 9/2014 | Blumrosen et al. | |
| 2014/0273858 A1 | 9/2014 | Panther et al. | |
| 2014/0275850 A1 | 9/2014 | Venkatraman et al. | |
| 2014/0275852 A1 | 9/2014 | Hong et al. | |
| 2014/0327515 A1 | 11/2014 | Luna et al. | |
| 2015/0026647 A1 | 1/2015 | Park et al. | |
| 2015/0035643 A1 | 2/2015 | Kursun | |
| 2015/0070134 A1 | 3/2015 | Nagisetty et al. | |
| 2015/0119728 A1 | 4/2015 | Blackadar et al. | |
| 2015/0161876 A1 | 6/2015 | Castillo | |
| 2015/0168365 A1 | 6/2015 | Connor | |
| 2015/0220109 A1 | 8/2015 | von Badinski et al. | |
| 2015/0242605 A1 | 8/2015 | Du et al. | |
| 2015/0254575 A1 | 9/2015 | Nere et al. | |
| 2015/0272483 A1 | 10/2015 | Etemad et al. | |
| 2015/0301608 A1 | 10/2015 | Nagaraju et al. | |
| 2015/0305674 A1 | 10/2015 | McPherson et al. | |
| 2015/0342489 A1 | 12/2015 | Bhaumik et al. | |
| 2015/0342527 A1 | 12/2015 | Karnik et al. | |
| 2016/0063233 A1 | 3/2016 | Bae et al. | |
| 2016/0154952 A1 | 6/2016 | Venkatraman et al. | |
| 2016/0189451 A1 | 6/2016 | Yoo et al. | |
| 2016/0191517 A1 | 6/2016 | Bae et al. | |
| 2016/0313176 A1 | 10/2016 | Lee | |
| 2016/0378235 A1 | 12/2016 | Dow et al. | |
| 2017/0000415 A1 | 1/2017 | Lapetina et al. | |
| 2017/0011210 A1 | 1/2017 | Cheong et al. | |
| 2017/0032168 A1 | 2/2017 | Kim | |
| 2017/0035327 A1 | 2/2017 | Yuen et al. | |
| 2017/0035328 A1 | 2/2017 | Yuen et al. | |

(56) References Cited

U.S. PATENT DOCUMENTS

| | | | |
|---|---|---|---|
| 2017/0038848 A1 | 2/2017 | Yuen et al. | |
| 2017/0039358 A1 | 2/2017 | Yuen et al. | |
| 2017/0189755 A1 | 7/2017 | McKirdy et al. | |
| 2017/0231519 A1 | 8/2017 | Westover et al. | |
| 2017/0235935 A1 | 8/2017 | Song et al. | |
| 2017/0255273 A1 | 9/2017 | Yuen et al. | |
| 2018/0020984 A1* | 1/2018 | Hall | A61B 5/6806 600/301 |
| 2018/0067565 A1 | 3/2018 | Yuen et al. | |
| 2018/0296136 A1* | 10/2018 | Foxlin | G01G 19/50 |
| 2019/0050064 A1 | 2/2019 | Yuen et al. | |
| 2019/0215369 A1* | 7/2019 | Pry | G06F 9/445 |
| 2019/0251238 A1 | 8/2019 | Venkatraman et al. | |
| 2020/0167004 A1 | 5/2020 | Yuen et al. | |
| 2020/0260999 A1 | 8/2020 | Foxlin et al. | |

FOREIGN PATENT DOCUMENTS

| | | |
|---|---|---|
| WO | WO 12/170924 | 12/2012 |
| WO | WO 12/171032 | 12/2012 |
| WO | WO 15/127067 | 8/2015 |
| WO | WO 16/003269 | 1/2016 |

OTHER PUBLICATIONS

US Final Office Action, dated Apr. 25, 2017, issued in U.S. Appl. No. 15/231,620.

US Notice of Allowance, dated Feb. 23, 2017, issued in U.S. Appl. No. 15/231,636.

US Notice of Allowance, dated Oct. 23, 2017, issued in U.S. Appl. No. 15/603,305.

US Notice of Allowance, dated Jul. 6, 2018, issued in U.S. Appl. No. 15/812,879.

US Notice of Allowance, dated Jul. 25, 2019, issued in U.S. Appl. No. 16/153,618.

US Notice of Allowance, dated Oct. 26, 2020, issued in U.S. Appl. No. 16/663,166.

US Office Action, dated Dec. 19, 2016, issued in U.S. Appl. No. 15/231,636.

US Final Office Action, dated May 3, 2017, issued in U.S. Appl. No. 15/231,636.

US Office Action, dated Dec. 7, 2016, issued in U.S. Appl. No. 15/231,641.

US Final Office Action, dated Apr. 20, 2017, issued in U.S. Appl. No. 15/231,641.

US Office Action, dated Jan. 27, 2017, issued in U.S. Appl. No. 15/012,607.

US Final Office Action, dated May 16, 2017, issued in U.S. Appl. No. 15/012,607.

US Office Action, dated Mar. 15, 2018, issued in U.S. Appl. No. 15/012,607.

US Office Action, dated Jun. 27, 2019, issued in U.S. Appl. No. 15/486,208.

US Notice of Allowance, dated Dec. 19, 2019, issued in U.S. Appl. No. 15/486,208.

US Notice of Allowance, dated Jun. 4, 2020, issued in U.S. Appl. No. 16/829,658.

Lara et al. (2013) "A Survey on Human Activity Recognition using Wearable Sensors," IEEE Communications Surveys & Tutorials, Third Quarter 2013, 15(3):1192-1207.

Mills, C. (2015) "Paying for stuff with your heartbeat is now a thing," GIZMODO (Published online, Aug. 12, 2015), 2pp.

Saeb Sohrab, et al. "Making Activity Recognition Robust against Deceptive Behavior," Dec. 11, 2015, PLoS ONE. (Year: 2015).

Terry, Ian Michael et al. "GeoFit: Verifiable Fitness Challenges," 2014 IEEE 11th International Conference on Mobile Ad Hoc and Sensor Systems. (Year: 2014).

U.S. Appl. No. 16/829,659, filed Mar. 25, 2020, Foxlin et al.

* cited by examiner

USER IDENTIFICATION BY BIOMETRIC MONITORING DEVICE

INCORPORATION BY REFERENCE

An Application Data Sheet is filed concurrently with this specification as part of the present application. Each application that the present application claims benefit of or priority to as identified in the concurrently filed Application Data Sheet is incorporated by reference herein in its entirety and for all purposes.

TECHNICAL FIELD

This disclosure relates to the field of biometric monitoring devices, and particularly to the identification of a user of a biometric monitoring device.

BACKGROUND

Consumer interest in personal health has led to a variety of personal health monitoring devices being offered on the market. Such devices, until recently, tended to be complicated to use and were typically designed for use with one activity, for example, bicycle trip computers.

Advances in sensors, electronics, and power source miniaturization have allowed the size of personal health monitoring devices, also referred to herein as "biometric tracking," "biometric monitoring," or, in certain embodiments, simply "wearable" devices, to be offered in extremely small sizes that were previously impractical. The number of applications for these devices is increasing as the processing power and component miniaturization for wearable devices improves.

Certain biometric monitoring devices may be configured to monitor biometrics from a plurality of users. A user may be required to select a corresponding user profile to ensure that the biometric measurements are associated with the correct user of the device. Thus, the user may be required to perform certain interactions with the biometric monitoring device in order to have the measured biometrics associated with the correct user profile.

SUMMARY

The systems, methods and devices of this disclosure each have several innovative aspects, no single one of which is solely responsible for the desirable attributes disclosed herein.

In one aspect, there is provided a method of operating a biometric monitoring device, the device comprising a platform configured to receive at least one foot of a user, a plurality of sensors, a memory, and processing circuitry. The method may involve: detecting that the user is standing on the platform; measuring, based on body-weight data generated by a first one of the sensors, a weight of the user in response to detecting that the user is standing on the platform; and determining, based on sensor data generated by a second one of the sensors, a user parameter indicative of the user's identification. The method may also involve: comparing the user parameter to a plurality of parameter values respectively associated with a plurality of user profiles stored in the memory; and comparing the measured weight of the user to a plurality of weight values respectively associated with each of the user profiles. The method may further involve: identifying the one of the user profiles as corresponding to the user based on the comparison of the user parameter to the parameter values and the comparison of the measured weight of the user to the weight values; and updating the identified user profile based on at least one of the measured weight and the user parameter.

In another aspect, there is provided a biometric monitoring device that includes: a platform configured to receive at least one foot of a user; a first sensor configured to generate body-weight data; a second sensor configured to generate sensor data; and a memory configured to store a plurality of user profiles, each user profile including a weight value and a parameter value. The biometric monitoring device may further include processing circuitry configured to: detect that the user is standing on the platform; measure, based on the body-weight data generated by the first sensor, a weight of the user in response to detecting that the user is standing on the platform; determining, based on the sensor data generated by the second sensor, a user parameter indicative of the user's identification; comparing the user parameter to a plurality of parameter values respectively associated with a plurality of user profiles; comparing the measured weight of the user to a plurality of weight values respectively associated with each of the user profiles; identifying one of the user profiles as corresponding to the user based on the comparison of the user parameter to the parameter values and the comparison of the measured weight of the user to the weight values; and updating the identified user profile based on at least one of the measured weight and the user parameter.

In yet another aspect, there is provided a method of operating a biometric monitoring device, the device comprising a platform configured to receive at least one foot of a user, a body-weight sensor, a bioelectrical impedance sensor, a memory, and processing circuitry. The method may involve: detecting that the user is standing on the platform; measuring, based output from the body-weight sensor, a weight of the user in response to detecting that the user is standing on the platform; applying at least one electrical signal to the user's body; measuring, based on output from the bioelectrical impedance sensor, the bioelectrical impedance of the user's body based on the application of the at least one electrical signal; determining at least one bioelectrical impedance parameter associated with the user based on the measured bioelectrical impedance of the user's body according to a bioelectrical model of the user's body as a plurality of electrical elements; and identifying one of a plurality of user profiles as corresponding to the user based on the determined at least one bioelectrical impedance parameter.

DETAILED DESCRIPTION

One of the biometrics which may be measured and tracked by a biometric monitoring device is the weight of a user. Since changes to a user's weight outside of normal daily fluctuations occur at a relatively slow pace (e.g., on the order of days/weeks), a body-weight monitoring device (e.g., a scale) may be used by a user at relatively infrequent intervals (e.g., once a day). A user does not need to continually update their weight measurements over the course of the day (e.g., a user does not typically measure changes in weight over the course of a workout), and multiple users can measure their weight by sharing use of the same body-weight monitoring device.

When a plurality of users measure their respective body-weights using the same body-weight biometric monitoring device, it may be necessary to determine to which user a particular weight measurement corresponds in order to update the correct user's body-weight profile. One technique for distinguishing between users may involve receiving a selection and/or confirmation from the user to identify the correct user profile. However, it may be desirable to automatically identify the user in order to streamline the user's interaction with the body-weight biometric monitoring device (e.g., by simplifying and/or streamlining user identification and/or body weight measurement).

The difficultly in automatically distinguishing between two users may be related to the difference in weight between the two users. For example, when the difference in weight between two users is less than a predetermined value (e.g., 5 pounds), the normal fluctuations in weight of the users may result in overlapping body-weight measurements for the two users. Accordingly, it may not be possible to determine to which of the users a particular measurement belongs based solely on the body-weight measurement. Aspects of the present disclosure relate to techniques for identifying a user to which a particular body-weight measurement belongs by using additional information about the user.

Biometric Monitoring Device Overview

Figure 1A:
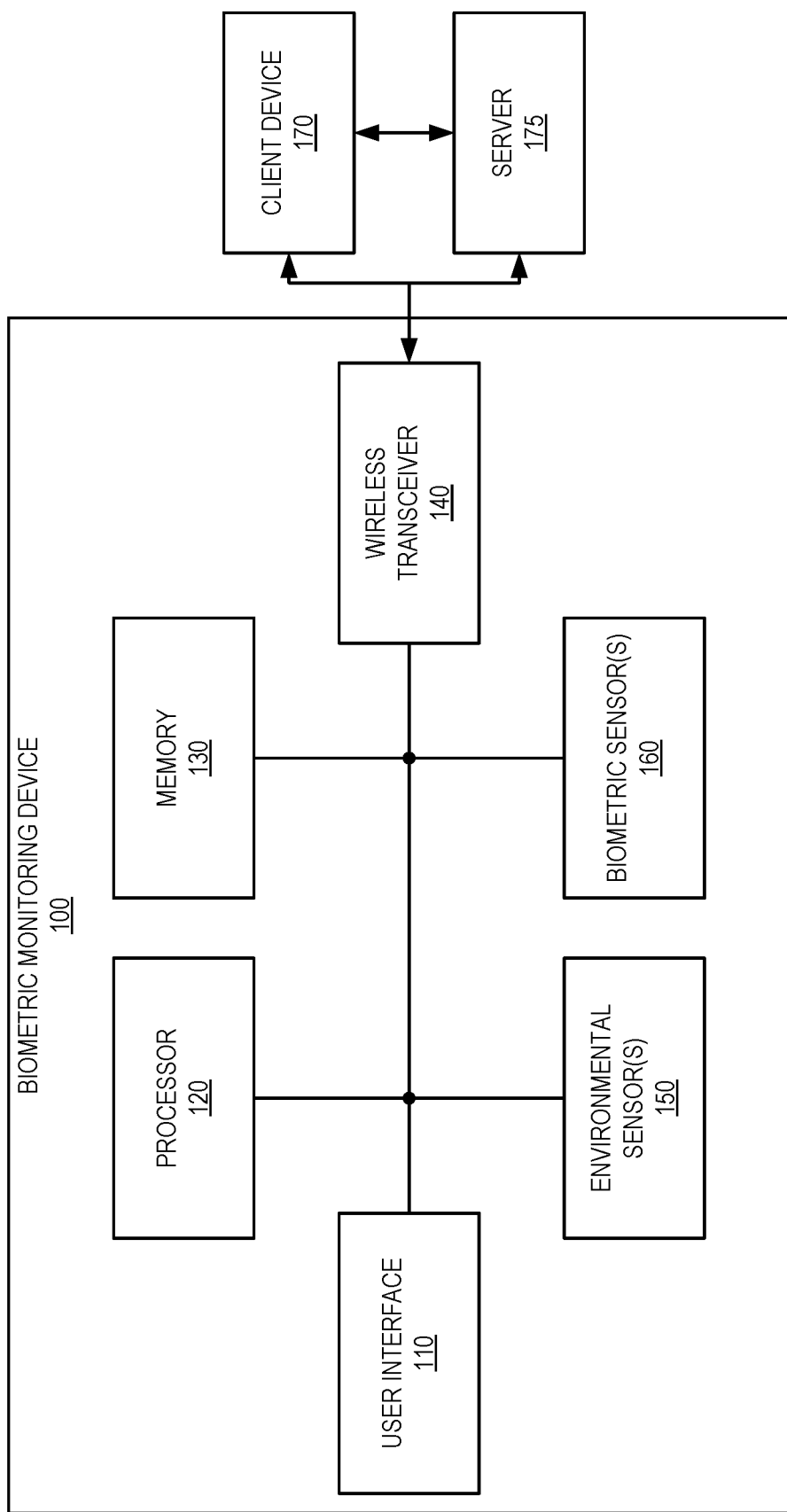
FIG. 1A is a block diagram illustrating certain components of an example biometric monitoring device in accordance with aspects of this disclosure.

FIG. 1A is a block diagram illustrating an example biometric monitoring device in accordance with aspects of this disclosure. The biometric monitoring device 100 may include a processor 120, a memory 130, a wireless transceiver 140, and one or more biometric sensor(s) 160. The biometric monitoring device 100 may also optionally include a user interface 110 and one or more environmental sensor(s) 150. Although certain block(s) and/or step(s) may be described as optional in connection with the description of the figures, depending on the embodiment, any one or more of the illustrated block(s) and/or step(s) may be optional (e.g., omitted) for certain embodiment(s). The wireless transceiver 140 may be configured to wirelessly communicate with a client device 170 and/or server 175, for example, either directly or when in range of a wireless access point (not illustrated) (e.g., via a personal area network (PAN) such as Bluetooth pairing, via a WLAN, via IEEE 802.11 (Wi-Fi), via near field communication (NFC), via one of the IEEE 802.15.4, ANT+, and ISO 18000-6C standards, etc.). Examples of the client device 170 include a wearable device (e.g., wearable device 302 illustrated in FIG. 3), a mobile phone, wired or wireless headphones, a music/media player (e.g., a portable music player), a camera, a weight scale, etc. Depending on the implementation, the client device 170 may be any device capable of communicating with the biometric monitoring device 100. Each of the memory 130, the wireless transceiver 140, the one or more biometric sensor(s) 160, the user interface 110, and/or the one or more environmental sensor(s) 150 may be in electrical communication with the processor 120.

The memory 130 may store instructions for causing the processor 120 to perform certain actions. For example, the processor 120 may be configured to measure a body-weight of a user and automatically determine to which of a plurality of user profiles the body-weight measurement corresponds. In some embodiments, the biometric sensors 160 may include one or more of a body-weight sensor, a bioelectrical impedance (also referred to as bio-impedance) sensor, an optical sensor (e.g., a photoplethysmographic (PPG) sensor), an accelerometer, a footprint scanner, and/or other biometric sensor(s). Further information regarding such biometric sensors are described in more detail below (e.g., in connection with FIG. 1B).

The biometric monitoring device 100 may collect one or more types of physiological and/or environmental data from the one or more biometric sensor(s) 160, the one or more environmental sensor(s) 150, and/or external devices and communicate or relay such information to other devices (e.g., the client device 170 and/or the server 175), thus permitting the collected data to be viewed, for example, using a web browser or network-based application. For example, while the user stands on the biometric monitoring device 100, the biometric monitoring device 100 may perform biometric monitoring via measuring the user's body-weight using the one or more biometric sensor(s) 160. The biometric monitoring device 100 may transmit data representative of the user's body-weight to an account on a web service (e.g., www.fitbit.com), computer, mobile phone, and/or health station where the data may be stored, processed, and/or visualized by the user. The biometric monitoring device 100 may measure or calculate other physiological metric(s) in addition to, or in place of, the user's body-weight. Such physiological metric(s) may include, but are not limited to: body-fat; bio-impedance; heart rate; heartbeat waveform; heart rate variability; heart rate recovery; blood pressure; blood glucose; skin conduction; skin and/or body temperature; muscle state measured via electromyography; brain activity as measured by electroencephalography; weight; caloric intake; nutritional intake from food; medication intake; pH levels; hydration levels; respiration rate; and/or other physiological metrics.

The biometric monitoring device 100 may also measure or calculate metrics related to the environment around the user (e.g., with the one or more environmental sensor(s) 150), such as, for example, barometric pressure, weather conditions (e.g., temperature, humidity, pollen count, air quality, rain/snow conditions, wind speed), light exposure (e.g., ambient light, ultra-violet (UV) light exposure, time and/or duration spent in darkness), noise exposure, radiation exposure, and/or magnetic field. Furthermore, the biometric monitoring device 100 (and/or the client device 170 and/or the server 175) may collect data from the biometric sensor(s) 160 and/or the environmental sensor(s) 150, and may calculate metrics derived from such data. For example, the biometric monitoring device 100 (and/or the client device 170 and/or the server 175) may calculate the user's stress or relaxation levels based on a combination of heart rate variability, skin conduction, noise pollution, and/or sleep quality. In another example, the biometric monitoring device 100 (and/or the client device 170 and/or the server 175) may determine the efficacy of a medical intervention, for example, medication, based on a combination of data relating to medication intake, sleep, and/or activity. In yet another example, the biometric monitoring device 100 (and/or the client device 170 and/or the server 22) may determine the efficacy of an allergy medication based on a combination of data relating to pollen levels, medication intake, sleep and/or activity. These examples are provided for illustration only and are not intended to be limiting or exhaustive.

Figure 1B:
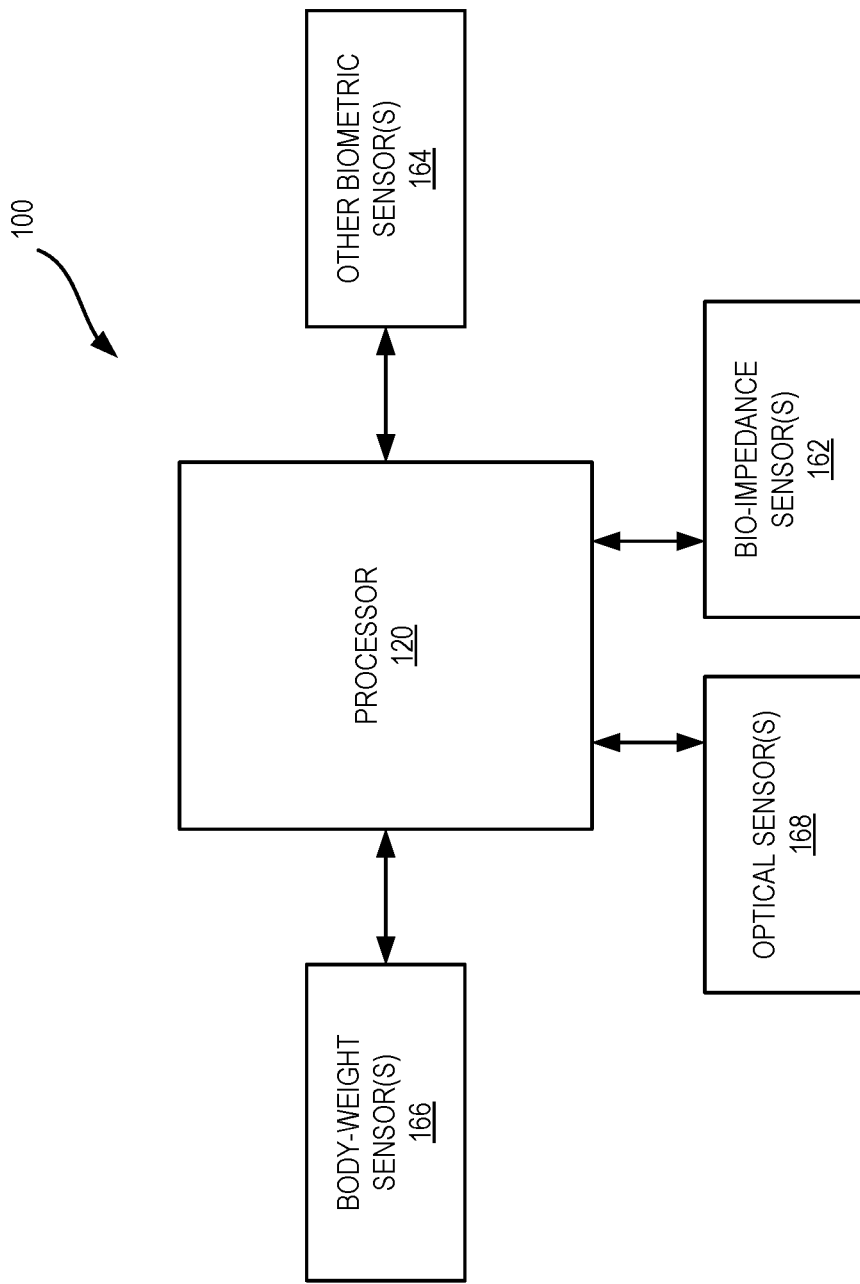
FIG. 1B is a block diagram illustrating example biometric sensors which may be in communication with a processor of a biometric monitoring device in accordance with aspects of this disclosure.

FIG. 1B is a block diagram illustrating a number of example biometric sensors that may be in communication with the processor of the biometric monitoring device in accordance with aspects of this disclosure. As used herein, the term biometric sensor 160 may generally refer to any sensor that senses or detects information about the user of the biometric monitoring device 100, as opposed to, for example, an environmental sensor 150 that senses or detects information about the environment rather than the user. For example, in the embodiment of FIG. 1B, the biometric monitoring device 100 may include one or more body-weight sensor(s) 166 which may be used to determine the body-weight of a current user of the biometric monitoring device 100. Examples of the body-weight sensor 166 include a load sensor, a piezoelectric sensor, a strain gauge, etc. In an example implementation, the body-weight sensor(s) 166 include a plurality of load sensors located at different positions in the biometric monitoring device 100. By including a plurality of load sensors, for example, located adjacent to the corners of the biometric monitoring device 100, the body-weight sensor(s) 166 may be able to determine the user's weight distribution (e.g., a pattern of motion of the user standing on a platform 195 of the biometric monitoring device 100 (see FIG. 1D)), which may be indicative of a center of the user's weight over the platform 195, while he/she is standing on the platform 195 and/or how the user's weight distribution changes while the user mounts the biometric monitoring device 100. The wearable device may further include bio-impedance sensor(s) 162 which may be used to determine the mass of the body-fat of the current user. The biometric monitoring device 100 may further include optional optical sensor(s) 168 (e.g., a PPG sensor), and may optionally include other biometric sensor(s) 164 such as directional sensor(s) (e.g., an accelerometer). Examples of directional sensor(s) include the accelerometer, gyroscopes, magnetometers, a 3-axis inertial-measurement unit (IMU), a 6-axis IMU, a 9-axis IMU, etc. For example, the 3-axis IMU may be an accelerometer, the 6-axis IMU may be a combination of an accelerometer and a gyroscope, and the 9-axis IMU may be a combination of an accelerometer, a gyroscope, and a magnetometer. Each of the biometric sensors illustrated in FIG. 1B is in electrical communication with the processor 120. The processor 120 may use input received from any combination of the body-weight sensor(s) 166, the optical sensor(s) 168, the bio-impedance sensor(s) 162, and/or the other biometric sensor(s) 164 in determining to which user profile a current body-weight measurement corresponds. In some embodiments, the body-weight sensor(s) 166, the optical sensor(s) 168, the bio-impedance sensor(s) 162, and/or the other biometric sensor(s) 164 may correspond to the biometric sensor(s) 160 illustrated in FIG. 1A.

Other examples of the biometric sensor(s) 160 include sensors to detect, measure and/or sense data which is representative of heart rate, respiratory rate, hydration, height, sun exposure, blood pressure and/or arterial stiffness. In addition thereto, or in lieu thereof, the biometric monitoring device 100 may detect, measure and/or sense (via appropriate sensors) other physiologic data. All such physiologic data or parameters, whether now known or later developed, are intended to fall within the scope of this disclosure. Similarly, although the biometric sensor(s) 160 may be depicted as independent, they may be collaborative and perform multiple types of measurements. For example, a body-weight sensor 166 in combination with bio-impedance sensor 162 may be used to measure body fat, hydration, and/or fat-free mass.

It related aspects, the processor 120 and other component(s) of the biometric monitoring device 100 (e.g., shown in FIGS. 1A and 1B) may be implemented as any of a variety of suitable circuitry, such as one or more microprocessors, application specific integrated circuits (ASICs), field programmable gate arrays (FPGAs), discrete logic, software, hardware, firmware or any combinations thereof. When the techniques are implemented partially in software, a device may store instructions for the software in a suitable, non-transitory computer-readable medium and execute the instructions in hardware using one or more processors to perform the techniques of this disclosure.

In further related aspects, the processor 120 and other component(s) of the biometric monitoring device 100 may be implemented as a SoC that may include one or more CPU cores that use one or more reduced instruction set computing (RISC) instruction sets, a WWAN radio circuit, a WLAN radio circuit, and/or other software and hardware to support the biometric monitoring device 100.

Figure 1C:
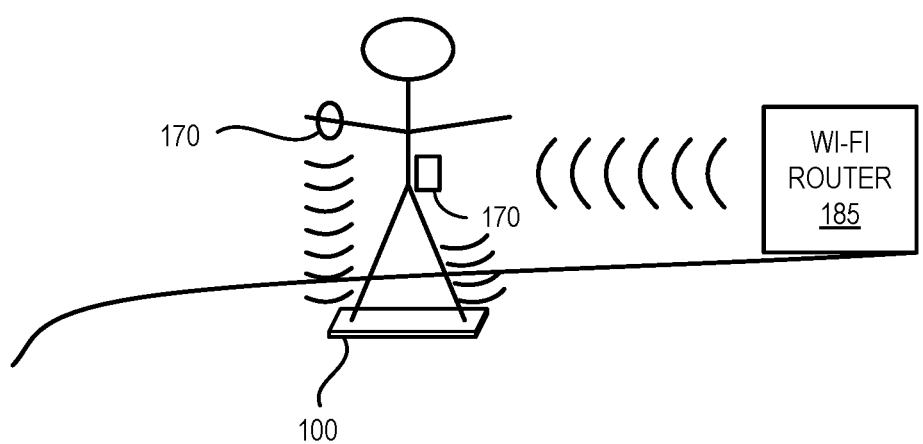
FIG. 1C is an example block diagram illustrating an ad-hoc communication network that may be used in determining a user profile to which a current body-weight measurement corresponds in accordance with aspects of this disclosure.

FIG. 1C is an example block diagram illustrating an ad-hoc communication network that may be used in determining a user profile to which a current body-weight measurement corresponds in accordance with aspects of this disclosure. As shown in FIG. 1C, a user is standing on a biometric monitoring device 100, is wearing a wearable device 170 on his/her wrist (e.g., the wearable device 302 illustrated in FIG. 3), and is carrying a mobile device 170. The biometric monitoring device 100, the wearable device, and/or the client device 170 may be in wireless communication with each other and/or a Wi-Fi router 185.

As described in more detail below, the biometric monitoring device 100 may determine a parameter which is indicative of the identity of the user based on sensor data generated by a sensor other than the body-weight sensor(s) 166. The parameter may be a physiological parameter or a non-physiological parameter. The sensor data may be generated by and/or received from at least one of the biometric monitoring device 100, the wearable device 170, the mobile device 170, and the Wi-Fi router 185. For example, in one implementation the biometric monitoring device 100 may receive the parameter indicative of the identity of the user from at least one of the wearable device 170, the mobile device 170, and the Wi-Fi router 185. Additionally, the biometric monitoring device 100 may log each of the body-weight measurements into a corresponding user account stored on a server 175 via the Wi-Fi router 185.

Figure 1D:
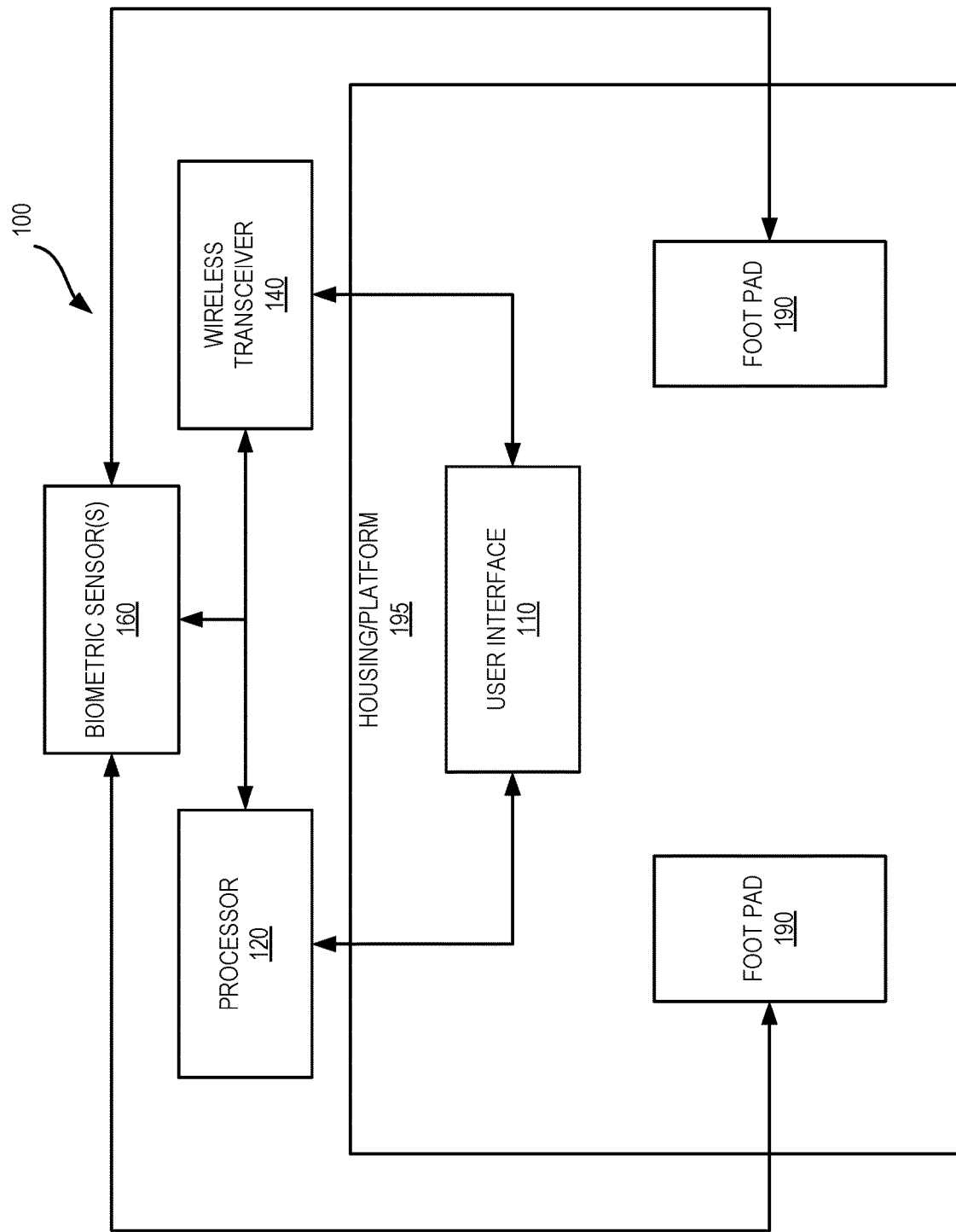
FIG. 1D is a block diagram illustrating certain components of another example biometric monitoring device in accordance with aspects of this disclosure.
Figure 2B:
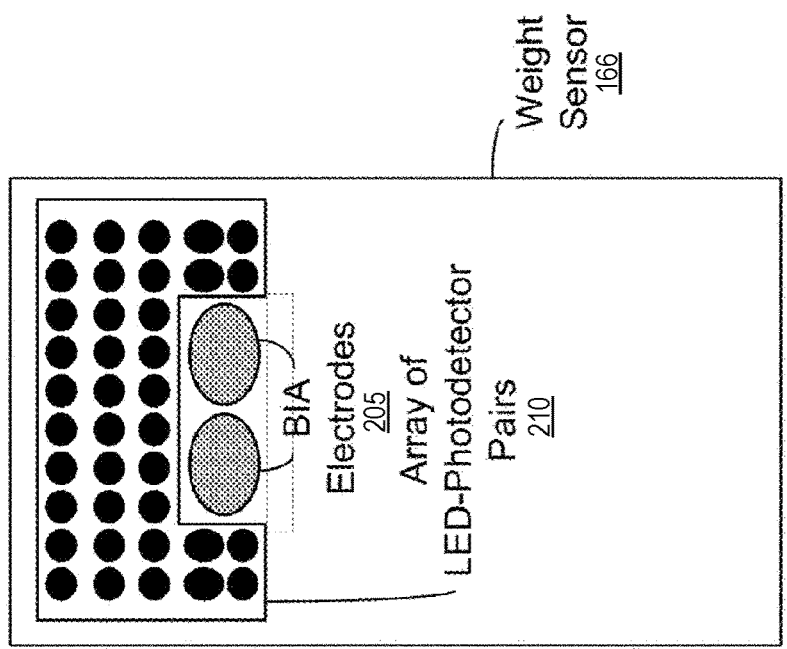
FIGS. 2A-2D are example layout configurations of physiological sensors (e.g., foot pads) of a biometric monitoring device in accordance with aspects of this disclosure.
Figure 2A:
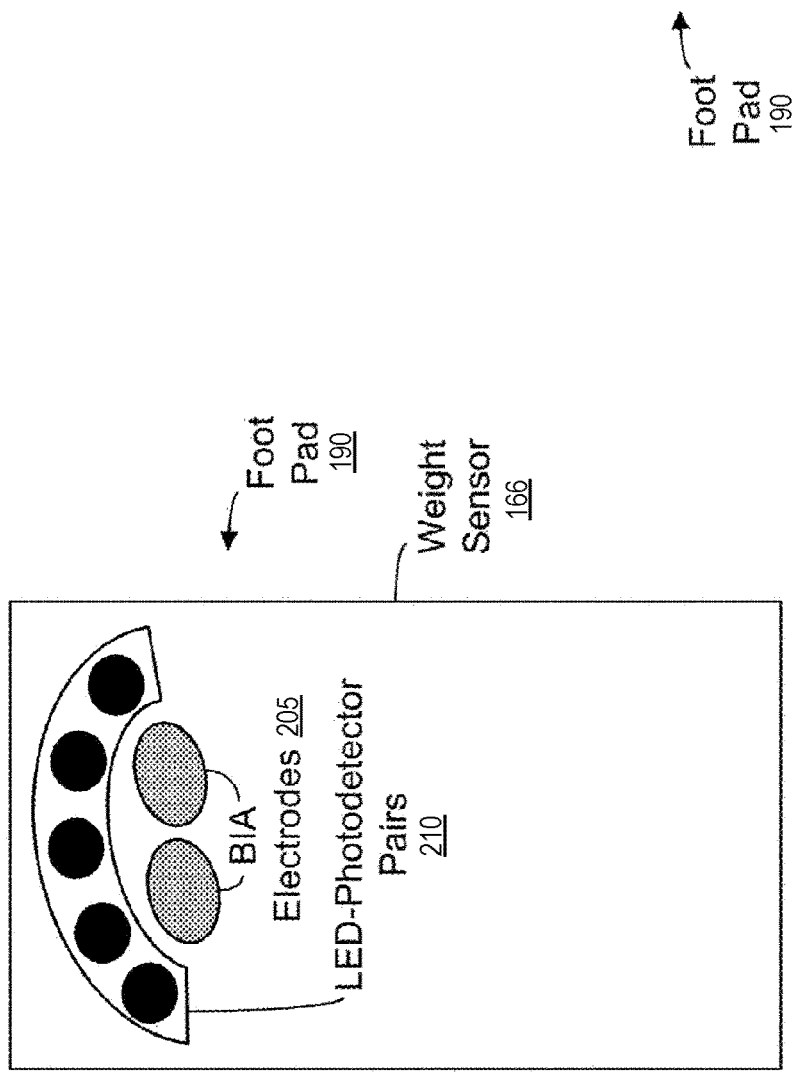
Figure 2D:
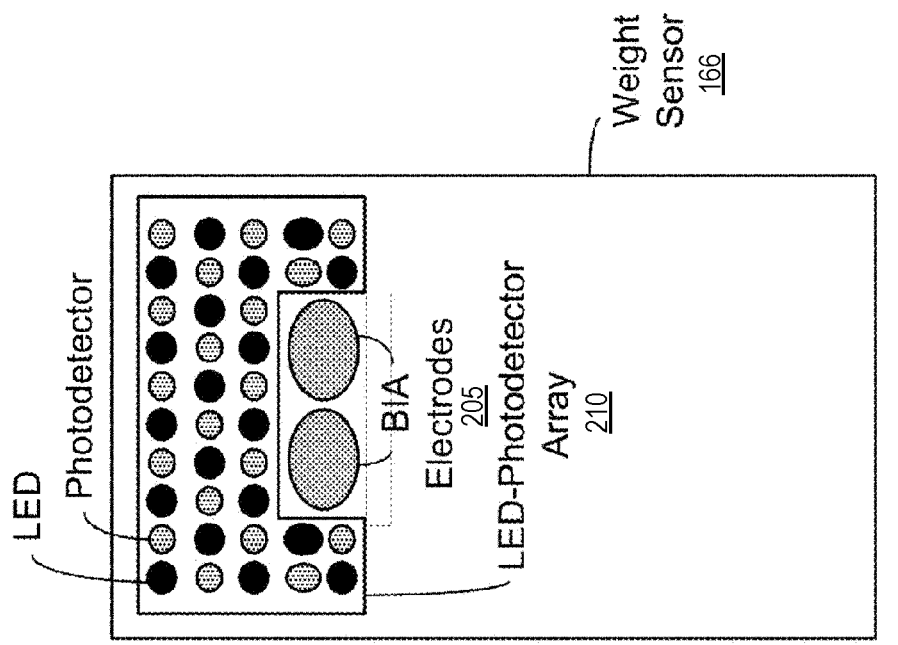
Figure 2C:
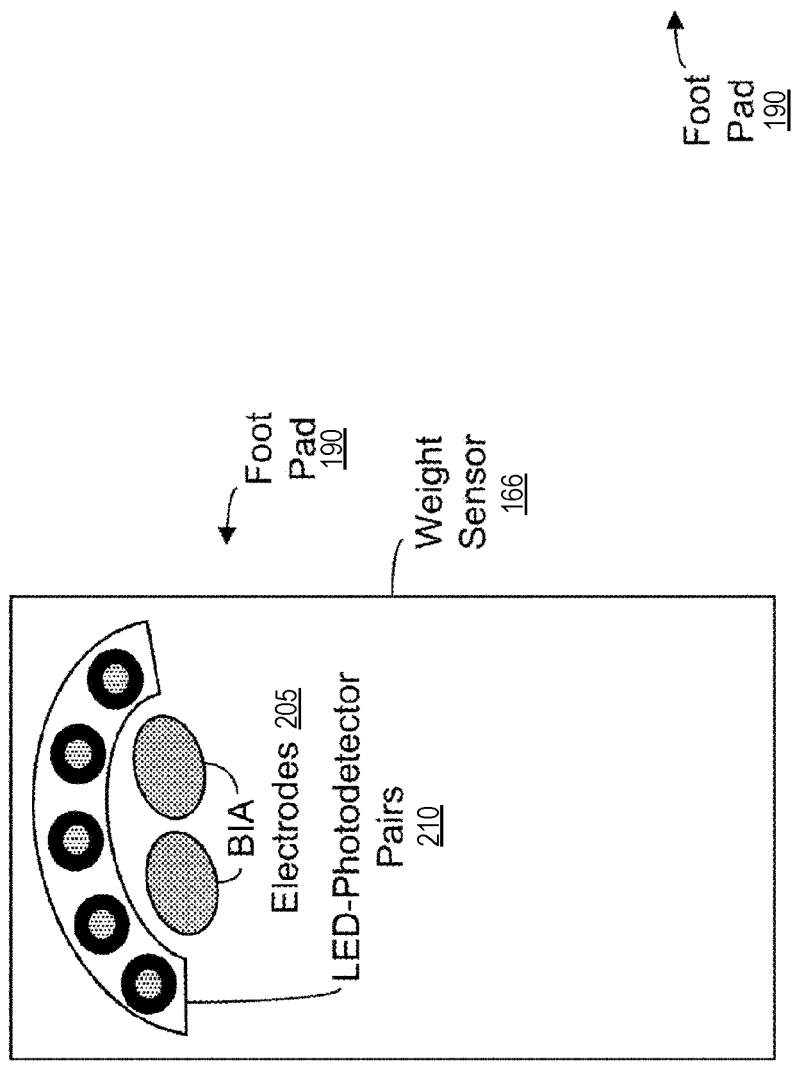

FIG. 1D a block diagram illustrating certain components of another example biometric monitoring device in accordance with aspects of this disclosure. As shown in FIG. 1D, the biometric monitoring device 100 may include a housing/platform 195 which houses the electronics and sensor(s) of the biometric monitoring device 100. The biometric monitoring device 100 may further include a processor 120, a wireless transceiver 160, and one or more biometric sensor(s) 160. The biometric sensor(s) 160 may be housed within the platform 195 and communicate with the processor 120 via a wired connection or may also be remote from the platform 195 and communicate with the processor 120 via the wireless transceiver 160.

In the illustrated embodiment, the biometric monitoring device 100 may also include a pair of foot pads 190 and a user interface 110, which may be positioned in the illustrated regions of the platform 195. The platform 195 may be configured to receive at least one foot of a user, for example, the platform 195 may be configured to receive the feet of a user at the respective foot pads 190. However, the described technology is not so limited and the foot pad(s) and/or user interface 110 may be located in other positions. For example, the biometric monitoring device 100 may use a user interface of a client device 100 (e.g., a mobile phone) as an interface for communication with the user.

The user interface 110 of biometric monitoring device 100 may provide or facilitate exchange of physiologic information and, in certain embodiments, other information or data. For example, biometric monitoring device 100 may include one or more displays to present physiologic information including, for example, current information, historical information, and/or comparison like information, for example, current information in view of historical information. The historical information or data may include, for example, historical body-weight and/or body-fat data measured by the biometric monitoring device 100 (which may be stored internally to and/or externally from biometric monitoring device 100), historical user activity data, food consumption data, and/or sleep data (which may be measured or monitored by other personal and/or portable devices (for example, the wearable device 302 illustrated in FIG. 3), historical user biometric or physiologic data (for example, heart rate, blood pressure, arterial stiffness, blood glucose levels, cholesterol, duration of TV watching, duration of video game play and/or mood). Such historical data may be presented in pictorial, graphical and/or textual form.

In addition to or in lieu of one or more displays, user interface 110 may include one or more speakers to provide the user with such physiologic data or information (whether current, historical or both) in aural form.

The user interface 110 may also include an input mechanism to facilitate input of, for example, user data, commands and/or selections. In one embodiment, the user may communicate with biometric monitoring device 110 via a user interface including, for example, a touch pad, touch screen, buttons, switches and/or knobs. In another embodiment, user interface 110 of a biometric monitoring device 100 includes one or more audio sensors to detect speech or sounds. In this way, for example, the user may input data, commands and/or selections to biometric monitoring device 100. For example, in response to speech or sounds from the user, biometric monitoring device 100 may determine or identify the appropriate user (for example, from a list stored therein) which facilitates correlation of physiologic data (acquired by the one or more physiological sensors) with a particular user.

Certain biometric sensor(s) 160 may be located directly beneath the foot pads 190. For example, certain biometric sensor(s) 160 may generate a signal that is supplied to the skin of the user and measure a response from the user in order to measure a corresponding biometric. As an example, a PPG sensor may generate an optical signal which is applied to the user's feet and may measure the light reflected from the user. This reflected signal may be used by the PPG sensor to measure one or more of the user's heart rate, heartbeat waveform; heart rate variability; heart rate recovery, etc. Similarly, a bio-impedance sensor may generate an electrical signal which may be applied to the user through the user's feet or another part of the user's body connected to an electrode. The bio-impedance sensor may measure a response to the applied electrical signal and model certain parameters of the user's body based on the measured signal. Further examples of the bio-impedance sensor are discussed in detail below.

Foot Pads for Biometric Monitoring Device

FIGS. 2A-2D are example configurations of physiological sensor layouts of foot pads of a biometric monitoring device 100 (for example, illustrated in FIG. 1D) having a plurality of physiological sensors including a body-weight sensor 166, one or more LED-photo detector pairs 210 and one or more bioelectrical impedance analysis (BIA) electrodes 205. Depending on the implementation, one or more of the LED-photo detector pairs 210 and the bioelectrical impedance analysis (BIA) electrodes 205 may not be included.

In one embodiment, in operation, the processor 120 calculates or determines the user's weight based on or using data from the body-weight sensor 166 incorporated and/or embedded in foot pads. In addition, the processor 120 may employ the data from a bio-impedance sensor(s) 162, to calculate or determine a user's body fat composition and/or body mass index. The bio-impedance sensor(s) 162 may comprise the BIA electrodes 205, from which a small current may be applied to the user's body and the characteristics of the return current measured in the electrodes may be representative of the body fat composition of the user. The processor 120, based on data acquired or detected by the BIA electrodes 205 and user information (e.g., height, age, and gender), may calculate or determine a user's body fat composition and/or body mass index With continued reference to FIGS. 2A-2D, the foot pads also include one or more LED-photo detector pairs 210 arranged therein such that when the user placing blood-perfused area of the foot (for example, the big toe) over the one or more LED-photo detector pairs 210, the biometric monitoring device 100 may implement or perform photo plethysmography to calculate, assess and/or determine blood pressure and/or arterial stiffness. For example, an array of LED-photo detector pairs 210 may be employed to adaptively determine which location on the foot provides the best plethysmography signal. Using data from the LED-photo detector pairs 210, the processor 120 may calculate, assess and/or determine other biometric or physiological quantities such as heart rate, blood pressure and/or arterial stiffness. That is, the processor 120 may employ data from a heart rate sensor to calculate, assess and/or determine the user's heart rate using, for example, ballistocardiography. Based on the output of such sensors, the processor 120 may calculate, assess and/or determine the user's heart rate and store and/or output such information (for example, to a display (user interface) or external to biometric monitoring device 100 via wireless transceiver 140).

Wearable Device Overview

Figure 3:
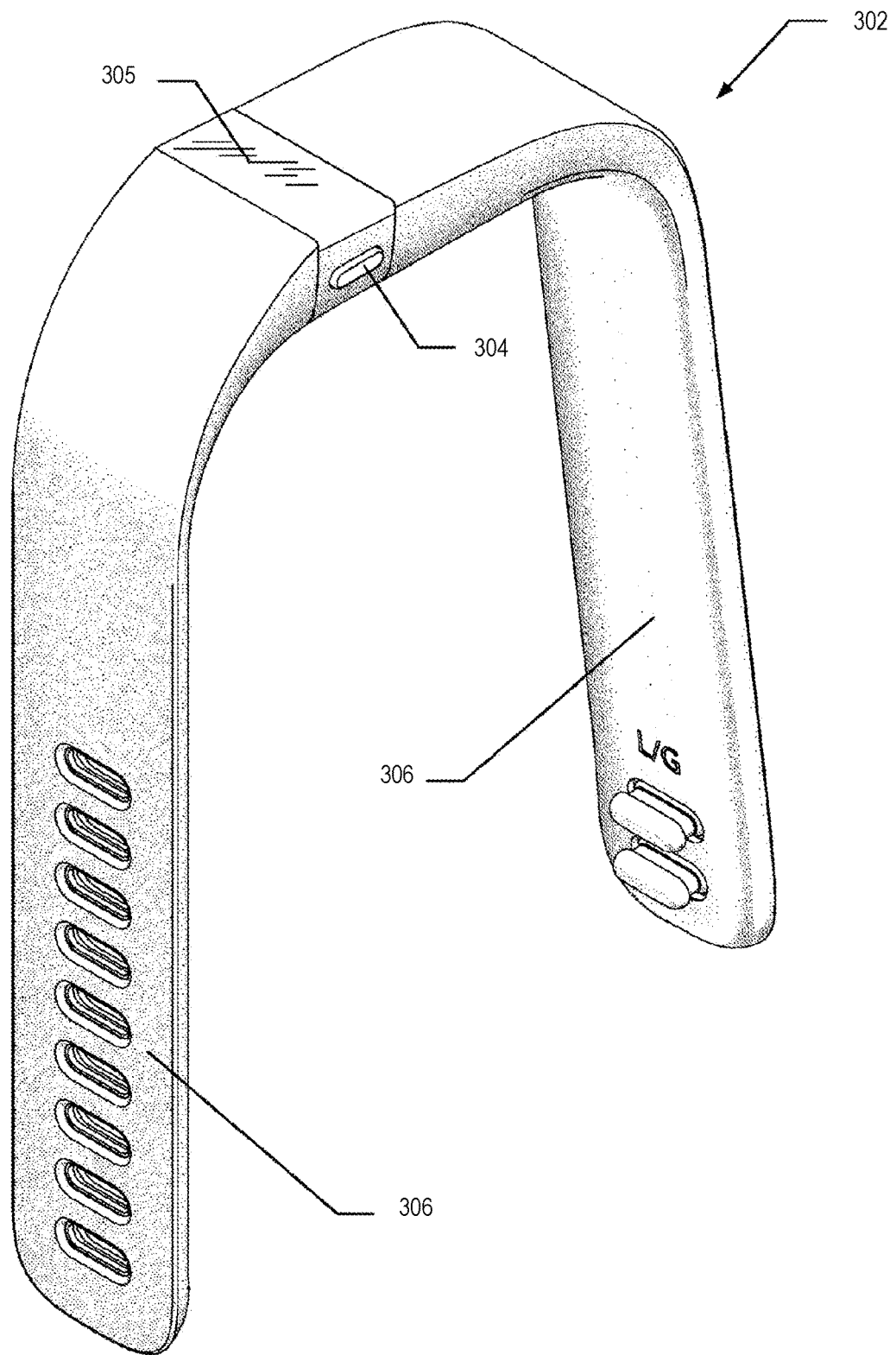
FIG. 3 is an example of a wrist-worn device in accordance with aspects of this disclosure.

In certain embodiments, the client device 170 may comprise a wearable device 302 which may have a shape and/or size adapted for coupling to (e.g., secured to, worn, borne by, etc.) the body or clothing of a user. FIG. 3 shows an example of a wrist-worn wearable device 302 in accordance with aspects of this disclosure. The wrist-worn wearable device 302 may have a display 305, button(s) 304, electronics package (not illustrated), and/or an attachment band 306. The attachment band 306 may be secured to the user through the use of hooks and loops (e.g., Velcro), a clasp, and/or a band having memory of its shape, for example, through the use of a spring metal band.

The wearable device 302 may collect one or more types of physiological and/or environmental data from one or more biometric sensor(s), one or more environmental sensor(s), and/or external devices and communicate or relay such information to other devices (e.g., the client device 170, the server 175, and or the biometric monitoring device 100), thus permitting the collected data to be viewed, for example, using a web browser or network-based application. For example, while being worn by the user, the wearable device 302 may perform biometric monitoring via calculating and storing the user's step count using one or more biometric sensor(s) included therein. The wearable device 302 may transmit data representative of the user's step count to an account on a web service (e.g., www.fitbit.com), computer, mobile phone, and/or health station where the data may be stored, processed, and/or visualized by the user. The wearable device 302 may measure or calculate other physiological metric(s) in addition to, or in place of, the user's step count. Such physiological metric(s) may include, but are not limited to: energy expenditure, e.g., calorie burn; floors climbed and/or descended; heart rate; heartbeat waveform; heart rate variability; heart rate recovery; location and/or heading (e.g., via a GPS, global navigation satellite system (GLONASS), or a similar system); elevation; ambulatory speed and/or distance traveled; swimming lap count; swimming stroke type and count detected; bicycle distance and/or speed; blood pressure; blood glucose; skin conduction; skin and/or body temperature; muscle state measured via electromyography; brain activity as measured by electroencephalography; weight; body fat; caloric intake; nutritional intake from food; medication intake; sleep periods (e.g., clock time, sleep phases, sleep quality and/or duration); pH levels; hydration levels; respiration rate; and/or other physiological metrics.

The wearable device 302 may also measure or calculate metrics related to the environment around the user (e.g., with one or more environmental sensor(s) included therein), such as, for example, barometric pressure, weather conditions (e.g., temperature, humidity, pollen count, air quality, rain/snow conditions, wind speed), light exposure (e.g., ambient light, ultra-violet (UV) light exposure, time and/or duration spent in darkness), noise exposure, radiation exposure, and/or magnetic field. Furthermore, the wearable device 302 (and/or the client device 170, the server 175 and/or the biometric monitoring device 100) may collect data from biometric sensor(s) and/or the environmental sensor(s), and may calculate metrics derived from such data. For example, the wearable device 302 (and/or the client device 170, the server 175, and/or the biometric monitoring device 100) may calculate the user's stress or relaxation levels based on a combination of heart rate variability, skin conduction, noise pollution, and/or sleep quality. In another example, the wearable device 302 (and/or the client device 170, the server 175, and/or the biometric monitoring device 100) may determine the efficacy of a medical intervention, for example, medication, based on a combination of data relating to medication intake, sleep, and/or activity. In yet another example, the wearable device 302 (and/or the client device 170, the server 175, and/or the biometric monitoring device 100) may determine the efficacy of an allergy medication based on a combination of data relating to pollen levels, medication intake, sleep and/or activity. These examples are provided for illustration only and are not intended to be limiting or exhaustive.

User Identification

Certain aspects of this disclosure relate to the identification of a user currently using the biometric monitoring device 100. As discussed above, since body-weight biometric monitoring devices 100 are not typically used continually over extended periods of time (e.g., for longer than 1 minute at a time), but rather are typically used intermittently for shorter periods of time (e.g., less than 1 minute), a single body-weight biometric monitoring device 100 may be used by a plurality of users. Aspects of this disclosure relate to techniques for automatically determining to which user profile a given measurement taken by the biometric monitoring device 100 corresponds.

While the embodiments described below generally relate to a body-weight biometric monitoring device 100, the techniques may also be extended to other biometric monitoring devices, such as client device 170, which are shared between users. For example, two or more users may share a wearable device, such as wearable device 302 in order to track certain exercise metrics. The use of sensor data generated by a secondary sensor in order to identify the current user of the biometric monitoring device 100 as described below may also be applied to wearable device 302.

Figure 4:
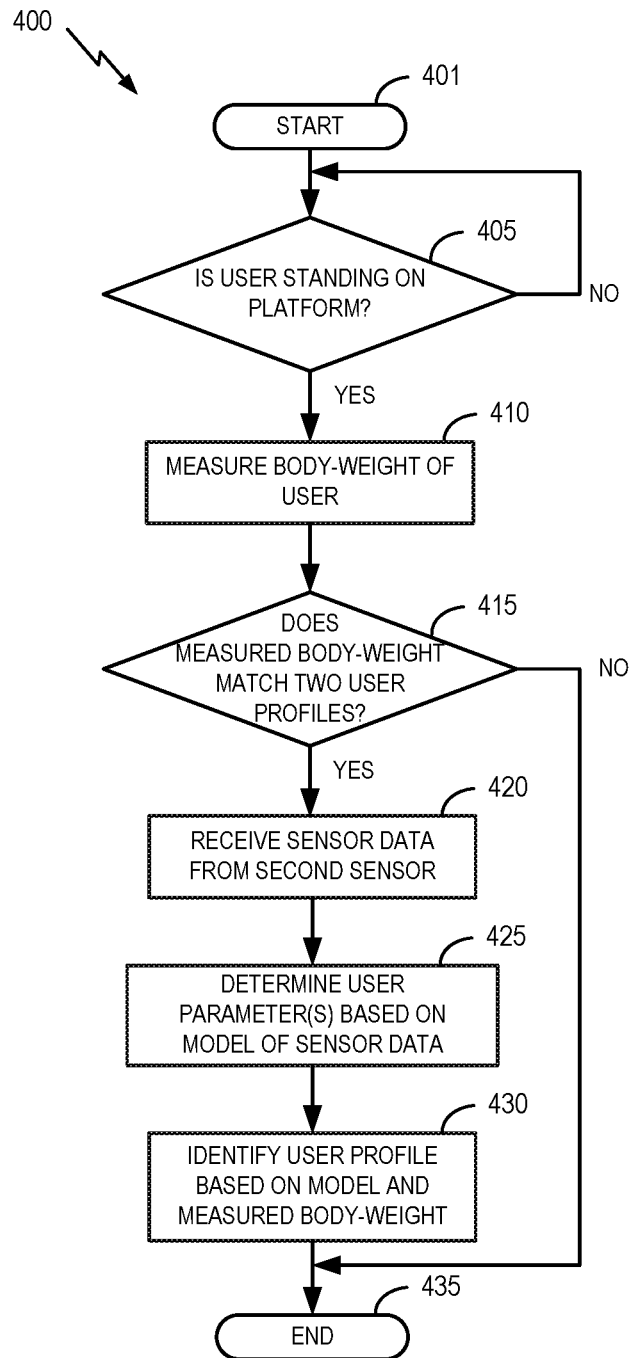
FIG. 4 is a flowchart illustrating a method for the automatic identification of a user of a biometric monitoring device in accordance with aspects of this disclosure.

FIG. 4 is a flowchart illustrating an example method for the automatic identification of a user of a biometric monitoring device in accordance with aspects of this disclosure. The method 400 may be operable by a biometric monitoring device 100, or component(s) thereof, for user identification in accordance with aspects of this disclosure. For example, the steps of method 400 illustrated in FIG. 4 may be performed by a processor 120 of the biometric monitoring device 100. In another example, a client device 170 (e.g., a mobile phone) or a server 175 in communication with the biometric monitoring device 100 may perform at least some of the steps of the method 400. For convenience, the method 400 is described as performed by the processor 120 of the wearable device 100.

The method 400 starts at block 401. At decision block 405, the processor 120 detects whether a user is standing on a platform 195 of the biometric monitoring device 100. In response to detecting that the user is not standing on the platform 195, the method 400 returns to the start of block 405. In response to detecting that the user is standing on the platform 195, the method 400 proceeds to block 410, at which the processor 120 measures the body-weight of the user using a body-weight sensor 166. At optional decision block 415, the processor 120 determines whether the measured body-weight matches two or more user profiles. For example, the processor 120 may determine whether the measured body-weight is within a defined range of two or more weight values associated with two or more corresponding user profiles stored in the memory 130. In some embodiments, memory 130 may correspond to volatile or non-volatile storage. In some embodiments, the user profiles stored in the memory 130 may be transmitted to the body-weight biometric monitoring device 100 from another device (e.g., a server) before, during, or after the body-weight of the user is measured at block 410. The weight values may be an average, mean, and/or other mathematical combination of the previous measured body-weight values for the corresponding user profiles. For example, the processor 120 may determine an expected body-weight value for each user profile based on a trend in the historical measured body-weight values for the given user.

In other embodiments, the processor 120 may determine whether the measured body-weight matches two or more user profiles by determining whether the measured body-weight is uniquely consistent with only one of the user profiles stored in the memory 130. For example, if the measured body-weight is not consistent with an expect amount of weight fluctuation since a previous body-weight measurement for a given user profile, the processor 120 may determine that the body-weight measurement is not consistent with the given user profile.

In yet other embodiments, the method 400 may proceed directly from block 410 to block 420. That is, the method 400 may include identifying a user profile corresponding to the user based on the measured body-weight and sensor data from a second sensor. The identification of a user profile will be described in greater detail below.

In response to the processor 120 determining that the measured body-weight matches two or more user profiles (yes from block 415) or in response to measuring the body-weight of the user (block 410), the method continues at block 420. In response to the processor 120 determining that the measured body-weight does not match two or more user profiles (no from block 415), the method 400 ends at block 435. At block 420, the processor 120 receives sensor data from a second sensor. For example, the processor 120 may receive sensor data from one or more of the optical sensor(s) 168, the bio-impedance sensor(s) 162, the environmental sensor(s) 150, and/or the other biometric sensor(s) 164.

At block 425, the processor 120 determines one or more user parameter(s) indicative of the user's identity. The determining of the user parameter(s) may be based on a model of the user generated from the received sensor data. For example, the processor 120 may determine a user parameter indicative of the user's identity based on the received sensor data by fitting the received sensor data to an electrical circuit model. Examples of data from which the user parameter may be determined include: bio-impedance data, footprint data, a unique client device 170 identifier, body-weight distribution data, a time of day of the weight measurement, a material worn on the user's feet during the weight measurement, a shape of the user's feet, etc.

At block 430, the processor 120 identifies one of the user profiles as corresponding to the user based on the parameter(s) and the measured weight. For example, the processor 120 may classify the measured body-weight as corresponding to the identified user profile based on the user parameter(s) matching the stored historic body-weight values for the identified user profile. As described in detail below, the matching of user parameter(s) to the stored historic body-weight values may involve determining a likelihood that the measured body-weight corresponds to each of the user profiles and selecting the user profile having the highest likelihood and/or confidence as the identified user profile. The method 400 ends at block 435. It is noted that the embodiments of the present disclosure are not limited to or by the example shown in FIG. 4, and other variations may be implemented without departing from the spirit of this disclosure.

Bio-Impedance

Figure 5:
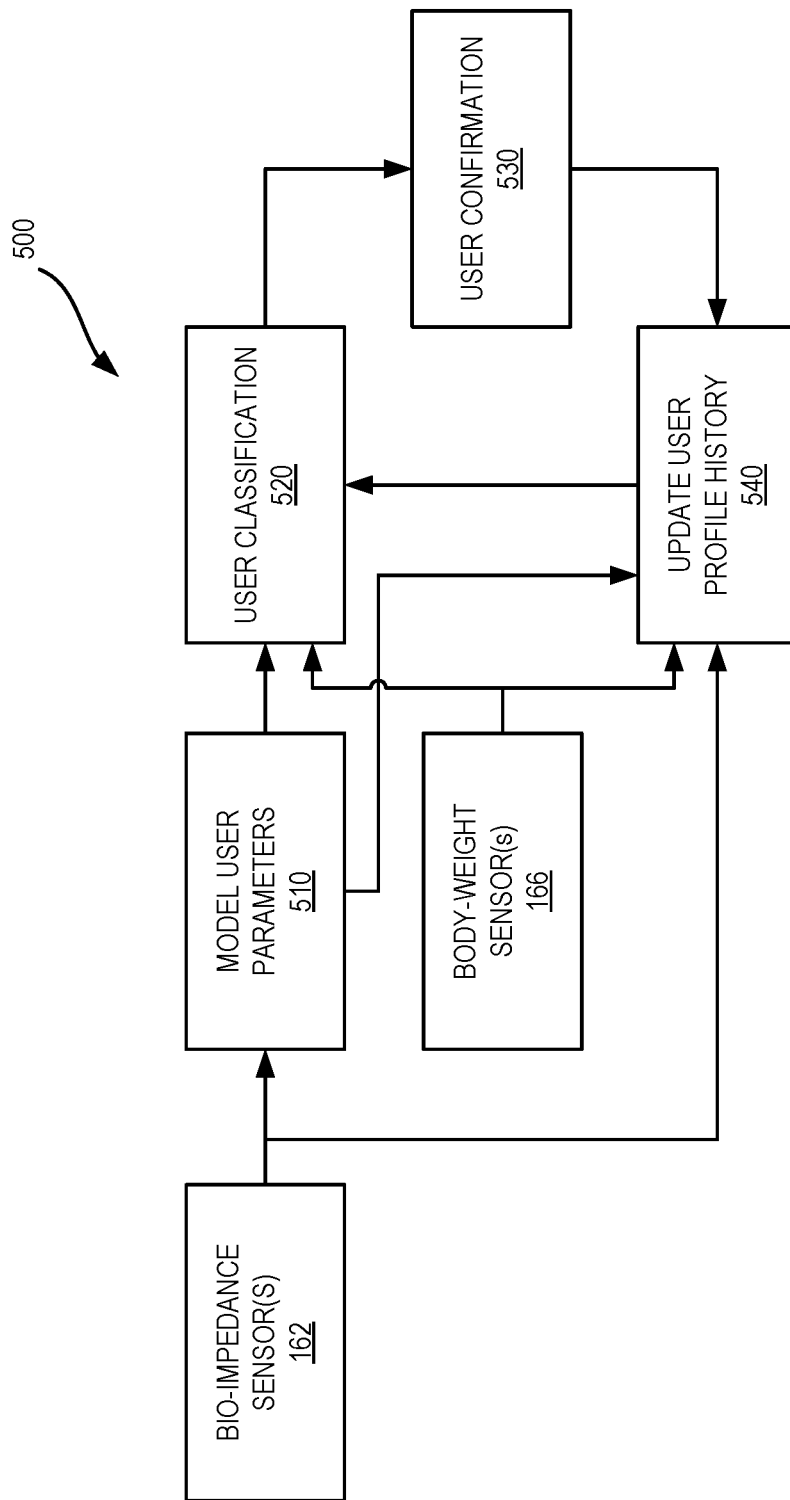
FIG. 5 is a block diagram illustrating an example method for classifying measurements in accordance with aspects of this disclosure.

FIG. 5 is a block diagram illustrating an example method for classifying measurements in accordance with aspects of this disclosure. The method 500 may be operable by a biometric monitoring device 100, or component(s) thereof, for user identification in accordance with aspects of this disclosure. For example, the steps of method 500 illustrated in FIG. 5 may be performed by a processor 120 of the biometric monitoring device 100. In another example, a client device 170 (e.g., a mobile phone) or a server 175 in communication with the biometric monitoring device 100 may perform at least some of the steps of the method 500. For convenience, the method 500 is described as performed by the processor 120 of the wearable device 100.

In the embodiment illustrated in FIG. 5, the method 500 may involve receiving data from body-weight sensor(s) 166 and bio-impedance sensor(s) 162. However, in other embodiments, aspects of the present disclosure may relate to methods which receive data from body-weight sensor(s) 166 and data from one or more other biometric sensor(s) 160, environmental sensor(s) 150, and/or wireless transceiver 140.

The bio-impedance sensor(s) 162 may include, for example, at least two electrodes, and in certain embodiments, may include at least four electrodes. In one embodiment, a first electrode (a source electrode) and a second electrode (a sink electrode) together apply an electrical signal to the user's body and a third electrode (a reference electrode) and a fourth electrode (a measurement point) together measure a response to the applied electrical signal. The electrodes may be positioned at different locations on the user's body such that the electrical signal flows through at least a portion of the user's body. In one implementation, the first and second electrodes may be located to contact a first foot of the user and the third and fourth electrodes may be located to contact a second foot of the user. In this implementation, the electrical signal may flow through the user's body between the feet of the user. In another implementation, the electrodes may be configured to apply the electrical signal to one portion of a user's foot and receive the electrical signal from another portion of the user's foot. For example, the first and second electrodes may be configured to contact the front portion of the user's foot (e.g., near the user's toes) while the third and fourth electrodes may be configured to contact a back portion of the user's foot (e.g., near the user's heel). In certain embodiments, four electrodes may be provided for each of the user's feet.

In other implementations, at least two of the electrodes may be configured to contact another portion of the user's body. For example, in certain implementations, the biometric monitoring device 100 may include a handle (not illustrated) which the user may grab with one or more of his/her hands. The first and second electrodes may be provided on the handle such that the electrical signal may be applied to the user and/or received from the user via the handle. Accordingly, the electrical signal may be applied to and/or received from one or more hands of the user.

Figure 7:
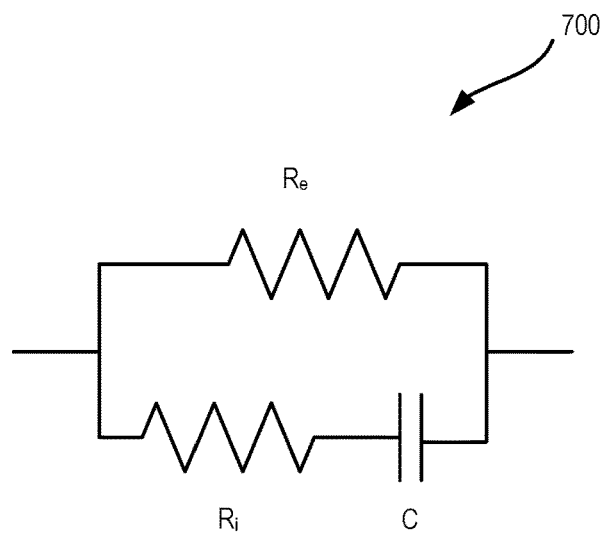
FIG. 7 is a diagram illustrating a circuit diagram model of the current paths illustrated in FIG. 6.

At block 510, the processor 120 receives bio-impedance data from one or more bio-impedance sensor(s) 162. The processor 120 fits the received bio-impedance data into a model of the human body to determine one or more parameters. The processor 120 may model the human body according to the model circuit 700 illustrated in FIG. 7. FIG. 7 is a circuit diagram model of the human body in accordance with aspects of this disclosure. As shown in FIG. 7, the human body may be modeled as an electrical circuit comprising two resistors $R_e$ and $R_i$ and a capacitor C. The circuit 700 may include an extracellular water pathway resistance $R_e$, an intracellular water resistance $R_i$, and a cell membrane capacitance C. For certain applications, the human body may be modeled as an electrical circuit where the extracellular water pathway resistance $R_e$ is formed in parallel with the intracellular water resistance $R_i$ and the cell membrane capacitance C. The equivalent impedance of the model circuit 700 may therefore be determined based on the following equation:

$$Z = \frac{R_e\left(R_i + \frac{1}{j\omega C}\right)}{R_e + \left(R_i + \frac{1}{j\omega C}\right)} \quad (1)$$

Figure 6:
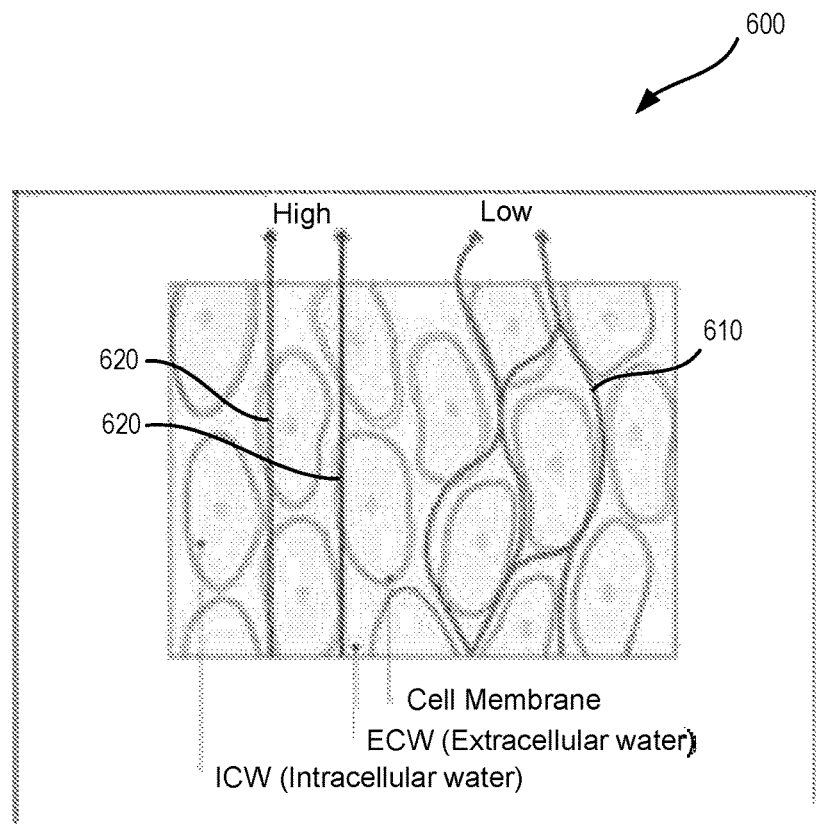
FIG. 6 is a diagram illustrating the various paths through which current may flow through the human body in accordance with aspects of this disclosure.

FIG. 6 is a diagram illustrating the various paths through which current may flow in connection with the circuit diagram model of FIG. 7. As shown in FIG. 6, low frequency current may be deflected around the cell membranes to flow through the extracellular water while high frequency current may pass through the cell walls and the intracellular water to flow through the user's tissue via a more direct path. The change in the current path may be modeled as proportional to the frequency of the current. One such model is given by equation (1) above. For example, a first current path 610 following the extracellular water pathway may be represented by a resistance $R_e$, while a second current path 620 passing through the intracellular water and the cell membranes may be represented by a parallel path including a resistance $R_i$ and a capacitance C. The resistance $R_i$ may a model of the intracellular water while the capacitance C may a model of the cell membranes. The values $R_e$, $R_i$, and C may be bioelectrical impedance parameters associated with the bio-impedance measurements of the user's body.

Based on one or more impedance measurements using the bio-impedance sensor(s) 162, the processor 120 may determine the values $R_e$, $R_i$, and C corresponding to the current user of the biometric monitoring device. When a plurality of impedance measurements are taken, at least three of the applied electrical signals may have different frequencies. One implementation for determining the values $R_e$, $R_i$, and C from a number of impedance measurements is shown below.

The magnitude of a given impedance measurement is given by:

$$|Z| = \frac{R_e\left|R_i + \frac{1}{j\omega C}\right|}{\left|R_e + R_i + \frac{1}{j\omega C}\right|} = \frac{R_e\sqrt{R_i^2 + \frac{1}{\omega^2 C^2}}}{\sqrt{R_e^2 + 2R_e R_i + R_i^2 + \frac{1}{\omega^2 C^2}}} \quad (2)$$

Based on equation (2), an observable value may be defined as:

$$y \equiv |Z|^2 = \frac{C_r^2 R_e^2 R_i^2 + R_e^2 x}{C_r^2(R_e^2 + 2R_e R_i + R_i^2) + x} = \frac{a+bx}{c+x}, \text{ where} \quad (3)$$

$$x \equiv \frac{1}{\omega^2 C_{nom}^2}$$

Here, $C_{nom}$ is a scaling factor which affects the stability of the equation and may be selected to aid in solving equation (3). By multiplying each side of equation (3) by (c+x), the equation can be altered to the form:

$$yx = a + bx - cy \quad (4)$$

Each of a plurality of measurements may be entered into equation (4) to generate a system of equations, which can be generalized by the following equation:

$$y^i x^i = [1 \; x^i \; -y^i]\begin{bmatrix} a \\ b \\ c \end{bmatrix} \quad (5)$$

From equation (5), the values represented by the vector $[a \; b \; c]^T$ may be solved for using, for example, a least squares approach, from which each of the values $R_e$, $R_i$, and C may be recovered.

Depending on the implementation, the bio-impedance sensor(s) 162 may be configured to apply one or more electrical signals to the user's feet, which may have differing frequencies. For example, since the user's body may be modeled as shown in FIG. 7 as an electrical circuit including three electrical components, the accuracy of the determination of the values $R_e$, $R_i$, and C may be increased by applying a greater number of electrical signals having different frequencies to make a greater number of measurements Z. However, embodiments of this disclosure may also relate to the application of a single electrical signal having one frequency.

In certain implementations, the bio-impedance sensor(s) 162 may apply a "white-noise" signal to the user and measure the electrical signal response. As used herein, a white-noise signal may refer to an electrical signal having a substantially uniform frequency distribution over a defined range of frequencies. In certain implementations employing a white-noise signal, rather than calculating values $R_e$, $R_i$, and C according to the model of FIG. 7, the processor 120 may log the electrical response signal as a parameter for user identification. For example, while the white-noise response signal may not necessarily contribute to an electrical circuit model of the human body, the white-noise response signal may be unique for different users, and thus, may be used by the processor 120 to construct a parameter history for user identification.

The user classification step 520 of FIG. 5 may be performed using the values $R_e$, $R_i$, and C along with the measured weight W. In one implementation, the processor 120 may format these values as a vector $(Z^{(i)} = [W, R_e, R_i, C]'$. The processor 120 may maintain a user profile for each of the users of the biometric monitoring device 100 in the memory 130. The user profile may be generated based on the history of measurements Z for the corresponding user. The user profile, including the history of measurements Z, may further be represented by a normal distribution for each of the parameters in the measurements Z, that is, the user profile may be represented by a multivariate normal distribution, which may be defined by its mean value μ and a covariance matrix Σ.

The relationship between a given measurement $Z^{(i)}$ and a user profile may be described by the Mahalanobis distance, which may be defined as the measure of the distance between the measurement $Z^{(i)}$ and the mean p of the user profile measurement history distribution, as scaled by the standard deviation. Mahalanobis distances may represent the likelihood that the measurement $Z^{(i)}$ belongs to the user profile. That is, a sample measurement having a first Mahalanobis distance to the mean $\mu_1$ of a first user profile than is less than a second Mahalanobis distance to the mean $\mu_2$ of a second user profile is more likely to belong to the first user profile than the second user profile. The Mahalanobis distance for a given measurement (e.g., a $k^{th}$ measurement) may be determined according to the following equation:

$$D_k^{(i)} = \sqrt{(Z^{(i)}-\mu_k)^T \Sigma_k^{-1} (Z^{(i)}-\mu_k)} \quad (6)$$

FIG. 7 is a plot of a plurality of measurements for two independent variables in accordance with aspects of this disclosure. In the example of FIG. 6, a plurality of Mahalanobis distance ellipses are overlaid to illustrate values of the standard deviation from the mean $\mu_k$ of the measurements. The likelihood of a given measurement $Z^{(i)}$ belonging to a user profile k may be given by the following equation:

$$L(Z^i | \mu_k, \Sigma_k) = \left((2\pi)^d * \left|\Sigma_k\right|\right)^{-\frac{1}{2}} * \exp\left(-\frac{1}{2}D_k^{(i)2}\right) \quad (7)$$

Additionally, a confidence that the given measurement $Z^{(i)}$ belongs to a user profile k may be defined as:

$$P(Z^{(i)} \in Z_k) = \frac{L(Z^{(i)} | \mu_k, \Sigma_k)}{\sum_j L(Z^{(i)} | \mu_j, \Sigma_j)} \quad (8)$$

The processor 120 may calculate a confidence P for each of the user profiles k that the given measurement $Z^{(i)}$ belongs to the corresponding user profiles k. The processor 120 may then determine whether the given measurement $Z^{(i)}$ belongs to one of the user profiles k based on the determined confidences P.

After a user profile k has been identified, the processor 120 may update the corresponding user profile history, as shown in block 540 of FIG. 5. The processor 120 may use a Kalman filter to update the identified user profile k with the current measurement $Z^{(i)}$. The use of the Kalman filter by the processor 120 may include a prediction of the current state of the user profile k using a dynamics model and processing the noise covariance of the user profile. The use of the Kalman filter may further involve updating the user profile k to correct the predicted current state using a measurement of noise information.

Weight Distribution

While the method of FIG. 5 was described above in connection with the use of bio-impedance measurements to determine the identity of the user of the biometric monitoring device 100, other implementations of the present disclosure relate to the use of alternative sensors/sources of data to determine the identity of the user. For example, in one implementation, the processor 120 may use additional data from the load sensors of the body-weight sensor(s) 166 to determine the identity of the user. In one implementation, the weight sensor(s) 166 comprise a plurality of load sensors (e.g., four load sensors) positioned under the platform 195 to track the position of the weight distribution on the platform 195. The number of load sensors may be less than or greater than four in other embodiments. Various different aspects of the user's weight distribution while the user is interacting with the biometric monitoring device 100 may be used by the processor to identify the user profile which corresponds to the user. For example, different aspects of the monitored weight distribution may be used as parameters by the processor 120 in distinguishing between user profiles, similar to the bio-impedance of the embodiments discussed in connection with FIGS. 5 to 7.

In one implementation, the processor 120 may track the weight distribution over the platform 195 as the user mounts the platform 195. This may involve tracking a position of the weight distribution (e.g., a center) from a measurement of zero body-weight until movement of the weight distribution settles to within a tolerance range for movement. That is, the weight distribution may be logged until changes in the weight distribution are less than a threshold change in distribution for longer than a predetermined period of time. Certain users may have a pattern in his/her mounting weight distribution which may distinguish the users from others. For example, one user may consistently mount the platform 195 with his/her left foot first before putting his/her right leg on the platform 195. Other mounting habits, such as an average weight distribution which is further forward, backward, left, and/or right compared to other users may be used to distinguish between users. The speed at which stabilization in the weight distribution is achieved may also be used to distinguish between users.

Figure 8:
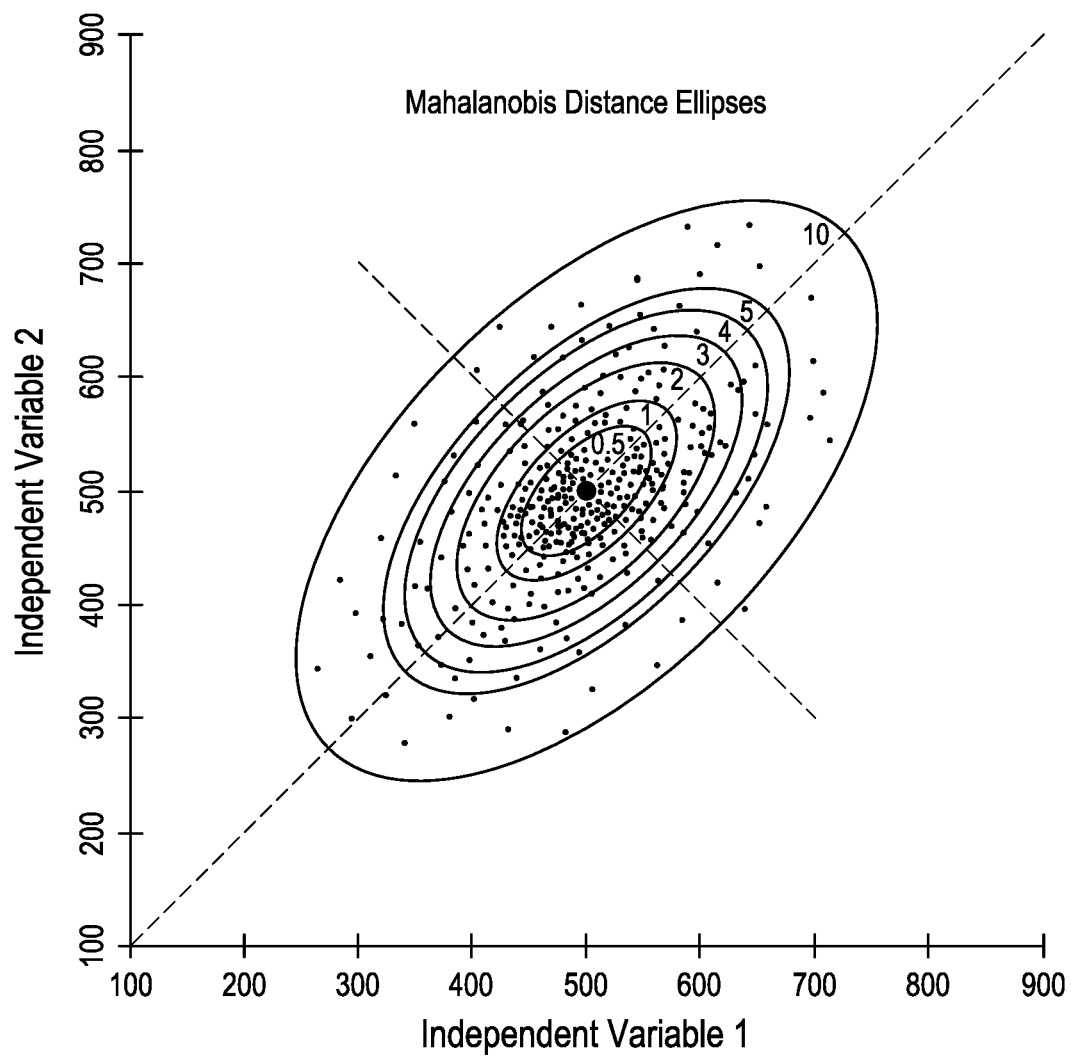
FIG. 8 is a plot of a plurality of measurements for two independent variables in accordance with aspects of this disclosure.

The processor 120 may also log the weight distribution of the user after the weight distribution has achieved stability (e.g., changes in the position of the weight distribution are less than the threshold change in distribution for longer than the predetermined period of time). Due to user preferences in position over the platform 195 and user posture habits, the location of the weight distribution after stabilization may not be centered on the platform 195. Thus, in certain implementations, the user profile may include a history measurements of the stabilized position of the center of the user's weight distribution. The weight distribution history may be analyzed for classification of the user measurement similar to the bio-impedance measurements as discussed in connection with FIG. 8.

In certain implementations, the body-weight sensor(s) 166 may further include one or more high-resolution pressure sensor(s). The high-resolution pressure sensor(s) may have a resolution that can determine an outline and/or pressure profile of the user's feet. Accordingly, the processor 120 may use one or more of the outline and pressure profile of the user's feet in determining the identity of the user.

Wireless Communication and Other User Identification Parameters

The processor 120 may also use other parameters in the identification of the user in addition to or in place of those discussed above. Further, in certain embodiments, the parameters may not be physiological parameters. For example, the processor 120 may use signals received via the wireless transceiver 140 to determine that a particular user is currently using the biometric monitoring device 100. That is, users of the biometric monitoring device 100 may wear and/or carry client devices 170, such as a wearable device 302 or a mobile phone which are associated with a particular user profile. These client devices 170 may wirelessly communicate with the processor 120 via the wireless transceiver 140 when within wireless communications range (e.g., the wearable device 302 and/or mobile phone may communicate with the wireless transceiver 140 via Bluetooth, Wi-Fi, NFC, etc.). Since one or more client device(s) 170 may be uniquely associated with a particular user, the processor 120 may identify the user of the biometric monitoring device 100 when the biometric monitoring device 100 is in communication with the client device(s) 170 while the biometric monitoring device 100 is measuring the body-weight of the user.

In one example, the processor 120 may establish wireless communication with a client device 170 when the user approaches the biometric monitoring device 100 and the user may subsequently mount the platform 195. After the user has completed measurement of his/her body-weight, the user may leave the wireless communication range of the wireless transceiver 140, thereby terminating communication between the processor 120 and the client device 170. Since the client device 170 was in wireless communication with the processor 120 during the measurement of the user's body-weight, the processor 120 may base the determination of the user profile corresponding to the user based on a unique identifier of the client device 170 (e.g., a device identifier such as media access control (MAC) address). The processor 120 may use the proximity of the client device 170 as a parameter for determining the user's identification. For example, the strength of the wireless communication signal between the client device 170 and the wireless transceiver 140 may be dependent on the distance between the client device 170 and the wireless transceiver 140. Accordingly, when two or more client devices 170 are in wireless communication with the wireless transceiver 140, the processor 120 may use the unique identifier of the client device 170 which is in closer proximity to the wireless transceiver 140 in determining the identity of the user.

Another parameter which may be used by the processor 120 in identifying the user is a footprint measurement of the user. For example, the biometric monitoring device 100 may include one or more optical sensor(s) 168, such as a footprint scanner. The footprint scanner may function similar to a fingerprint scanner and identify patterns in the ridges of the skin of the user's feet which may be used to identify the user. Depending on the implementation, the biometric monitoring device 100 may include two footprint scanners over in locations where the user places his/her feet when standing on the platform (see the footpads 190 of FIG. 1D). The footprint scanner may also identify when the user is wearing socks and/or shoes. Alternatively, the bio-impedance sensor(s) 162 may determine whether the user is wearing a material on his/her feet or whether the user has bare feet. The tendencies of the user to wear socks/shoes or use the scale with bare feet may be used as a parameter by the processor 120 to identify the user.

In certain implementations, the optical sensor(s) 168 may comprise a PPG sensor. The PPG sensor may be able to measure biometrics such as heart rate, heartbeat waveform, heart rate variability, heart rate recovery, etc. In other implementations, the bio-impedance sensor(s) 166 may be able to determine heart rate and/or blood pressure from the bio-impedance measurement. Any one of the parameters measured by optical sensor(s) 168 and/or bio-impedance sensor(s) 166 may be used by the processor 120 to determine the identity of the user.

In other implementations, the biometric monitoring device 100 may further include or be in wireless communications with a camera (e.g., the camera may be included in a smart mirror in wireless communication with the biometric monitoring device 100). The camera may be configured to identify users of the biometric monitoring device 100 based on facial recognition algorithms and/or other image processing that is substantially unique to the users of the biometric monitoring device 100. The processor 120 may use the facial recognition algorithms of the camera as a parameter in determining the identity of the user.

Automatic Determination of User Identification Parameters

A number of parameters which may be used by the processor 120 to identify the user of the biometric monitoring device 100 when the user is measuring his/her body-weight have been described. However, depending on the particular users who share a given biometric monitoring device 100, certain parameters may be more accurate in distinguishing between the users. Accordingly, in certain implementations, the processor 120 may identify those parameters which are more accurate in distinguishing and identifying the users of the biometric monitoring device 100 and track the histories of the identified parameters in the user profiles for user identification.

For example, the processor 120 may review the histories for each of the user profiles associated with the biometric monitoring device 100 to determine which user weight distribution parameters (e.g., habits) may be useful in distinguishing between the users of the biometric monitoring device. In one instance, a first user may habitually mount the biometric monitoring device 100 with his/her left foot and have a stabilized weight distribution which is forward from the center of the platform 195. A second user may habitually mount the biometric monitoring device 100 with his/her right foot and have a stabilized weight distribution which is to the right from the center of the platform 195. In this example, the processor 120 may identify the initial mounting foot and the stabilized weight distribution location as being parameters which may be used to distinguish between the users. The processor 120 may automatically identify users of the biometric monitoring device 100 based on the identified parameters.

As another example, the processor 120 may identify significant overlap in the bio-impedance histories stored in corresponding user profiles for two users. This overlap may make it difficult to distinguish between the two users when using the biometric monitoring device 100. In this example, the processor 120 may select one or more other parameters for identifying users including, for example, bio-impedance data, footprint data, a unique client device 170 identifier, body-weight distribution data, a time of day of the weight measurement, a material worn on the user's feet during the weight measurement, a shape of the user's feet.

Example Flowchart for User Identification By Biometric Monitoring Device

Figure 9:
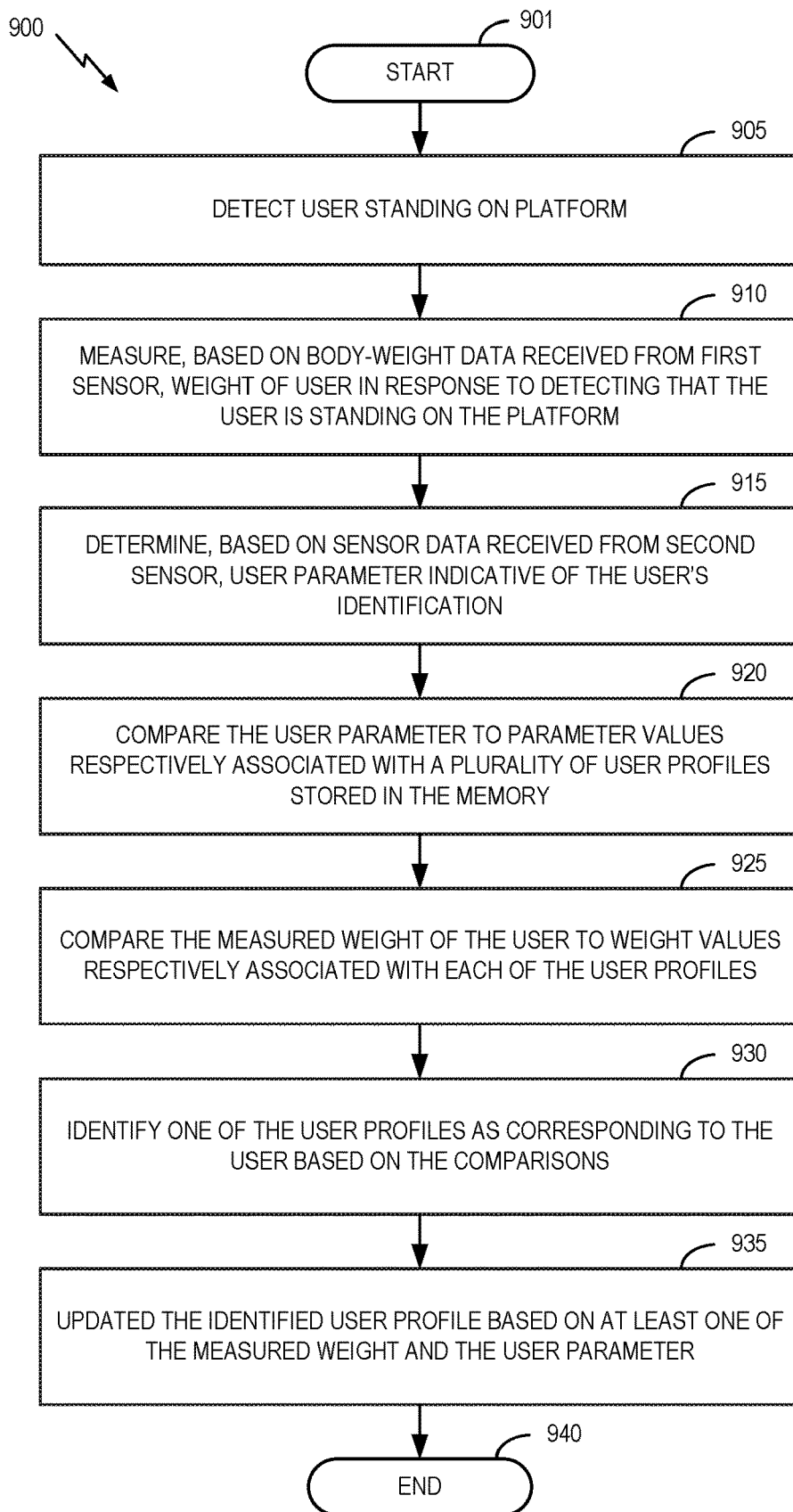
FIG. 9 is a flowchart illustrating an example method for user identification in accordance with aspects of this disclosure.

FIG. 9 is a flowchart illustrating an example method operable by a biometric monitoring device 100, or component(s) thereof, for user identification in accordance with aspects of this disclosure. For example, the steps of method 900 illustrated in FIG. 9 may be performed by a processor 120 of the wearable device 100. In another example, a client device 170 (e.g., a mobile phone or wearable device) or a server 175 in communication with the biometric monitoring device 100 may perform at least some of the steps of the method 900. For convenience, the method 900 is described as performed by the processor 120 of the biometric monitoring device 100.

In one implementation, the wearable device 100 comprises a platform 195 configured to receive at least one foot of a user, a plurality of sensors 140, 150, 160, a memory 130, and a processor (also referred to as processing circuitry) 120. The method 900 begins at block 901. At block 905, the processor 120 detects that the user is standing on the platform 195. At block 910, the processor 120 measures, based on body-weight data generated by a first one of the sensors, a weight of the user in response to detecting that the user is standing on the platform 195.

At block 915, the processor 120 determines, based on sensor data generated by a second one of the sensors, a user parameter indicative of the user's identification. In some embodiments, the determination of the parameter indicative of the user's identification may be in response to determining that the measured weight is within a defined range of two or more weight values. At block 920, the processor 120 compares the user parameter to a plurality of parameter values respectively associated with a plurality of user profiles stored in the memory. At block 925, the processor 120 compares the measured weight of the user to a plurality of weight values respectively associated with each of the user profiles. At block 930, the processor 120 identifies one of the user profiles as corresponding to the user based on the comparison of the user parameter to the parameter values and the comparison of the measured weight of the user to the weight values. At block 935, the processor 120 updates the identified user profile based on at least one of the measured weight and the user parameter. The method 900 ends at block 940. It is noted that the embodiments of the present disclosure are not limited to or by the example shown in FIG. 9, and other variations may be implemented without departing from the spirit of this disclosure.

Other Considerations

Information and signals disclosed herein may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

The various illustrative logical blocks, and algorithm steps described in connection with the embodiments disclosed herein may be implemented as electronic hardware, computer software, or combinations of both. To clearly illustrate this interchangeability of hardware and software, various illustrative components, blocks, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present disclosure.

The techniques described herein may be implemented in hardware, software, firmware, or any combination thereof. Such techniques may be implemented in any of a variety of devices, such as, for example, wearable devices, wireless communication device handsets, or integrated circuit devices for wearable devices, wireless communication device handsets, and other devices. Any features described as devices or components may be implemented together in an integrated logic device or separately as discrete but interoperable logic devices. If implemented in software, the techniques may be realized at least in part by a computer-readable data storage medium comprising program code including instructions that, when executed, performs one or more of the methods described above. The computer-readable data storage medium may form part of a computer program product, which may include packaging materials.

The computer-readable medium may comprise memory or data storage media, such as random access memory (RAM) such as synchronous dynamic random access memory (SDRAM), read-only memory (ROM), non-volatile random access memory (NVRAM), electrically erasable programmable read-only memory (EEPROM), FLASH memory, magnetic or optical data storage media, and the like. The techniques additionally, or alternatively, may be realized at least in part by a computer-readable communication medium that carries or communicates program code in the form of instructions or data structures and that can be accessed, read, and/or executed by a computer, such as propagated signals or waves.

Processor(s) in communication with (e.g., operating in collaboration with) the computer-readable medium (e.g., memory or other data storage device) may execute instructions of the program code, and may include one or more processors, such as one or more digital signal processors (DSPs), general purpose microprocessors, ASICs, field programmable logic arrays (FPGAs), or other equivalent integrated or discrete logic circuitry. Such a processor may be configured to perform any of the techniques described in this disclosure. A general purpose processor may be a microprocessor; but in the alternative, the processor may be any conventional processor, controller, microcontroller, or state machine. A processor may also be implemented as a combination of computing devices, for example, a combination of a DSP and a microprocessor, a plurality of microprocessors, one or more microprocessors in conjunction with a DSP core, or any other such configuration. Accordingly, the term "processor," as used herein may refer to any of the foregoing structure, any combination of the foregoing structure, or any other structure or apparatus suitable for implementation of the techniques described herein. Also, the techniques could be fully implemented in one or more circuits or logic elements.

The techniques of this disclosure may be implemented in a wide variety of devices or apparatuses, including a wearable device, a wireless handset, an integrated circuit (IC) or a set of ICs (e.g., a chip set). Various components, or units are described in this disclosure to emphasize functional aspects of devices configured to perform the disclosed techniques, but do not necessarily require realization by different hardware units. Rather, as described above, various units may be combined in a hardware unit or provided by a collection of inter-operative hardware units, including one or more processors as described above, in conjunction with suitable software and/or firmware.

Although the foregoing has been described in connection with various different embodiments, features or elements from one embodiment may be combined with other embodiments without departing from the teachings of this disclosure. However, the combinations of features between the respective embodiments are not necessarily limited thereto. Various embodiments of the disclosure have been described. These and other embodiments are within the scope of the following claims.

What is claimed is:

1. A method of operating a biometric monitoring device, the method comprising:

measuring, via a first sensor of a plurality of sensors of the biometric monitoring device, a weight of a user standing on a platform of the biometric monitoring device;

obtaining, via a transceiver of the biometric monitoring device, a user parameter from an electronic device associated with the user, the user parameter being specific to the user;

comparing the user parameter to a plurality of parameter values respectively associated with a plurality of user profiles stored in a memory of the biometric monitoring device;

comparing the measured weight of the user to a plurality of weight values respectively associated with the plurality of user profiles;

identifying a first user profile of the plurality of user profiles as corresponding to the user based on comparing the user parameter to the plurality of parameter values and comparing the measured weight to the plurality of weight values; and updating a weight value associated with the first user profile with the measured weight.

2. The method of claim 1, wherein the electronic device comprises a wearable electronic device.

3. The method of claim 2, wherein the user parameter comprises a device identifier that is specific to the wearable electronic device.

4. The method of claim 1, wherein the transceiver is configured to communicate with the electronic device via at least one of: Bluetooth, IEEE 802.11 (Wi-Fi), near field communication (NFC), IEEE 802.15.4, ANT+, and ISO 18000-6C.

5. The method of claim 1, wherein the first sensor comprises a pressure sensor.

6. The method of claim 1, wherein the electronic device comprises a mobile phone.

7. The method of claim 1, wherein obtaining the user parameter from the electronic device associated with the user occurs while the user is standing on the platform of the biometric monitoring device.

8. The method of claim 1, wherein obtaining the user parameter from the electronic device associated with the user occurs prior to measuring the weight of the user standing on the platform.

9. The method of claim 1, further comprising:
obtaining, by a second sensor of the plurality of sensors, biometric data associated with the user.

10. The method of claim 9, wherein the second sensor comprises an optical sensor.

11. The method of claim 10, wherein the optical sensor comprises a photoplethysmographic sensor.

12. A biometric monitoring device, comprising:
a platform configured to receive at least one foot of a user;
a first sensor configured to generate body-weight data;
transceiver;
a memory configured to store a plurality of user profiles, each user profile including a weight value and a parameter value; and
processing circuitry configured to:
measure, via the first sensor, a weight of the user when the user is standing on the platform;
obtain, via the transceiver, a user parameter from an electronic device associated with the user, the user parameter being specific to the user;
compare the user parameter to a plurality of parameter values respectively associated with the plurality of user profiles;
comparing the measured weight of the user to a plurality of weight values respectively associated with the plurality of user profiles;
identify a first user profile of the plurality of user profiles as corresponding to the user based on comparing the user parameter to the parameter values and comparing the measured weight to the plurality of weight values; and
update a weight value of the first user profile with the measured weight.

13. The biometric monitoring device of claim 12, wherein the electronic device associated with the user comprises a wearable electronic device.

14. The biometric monitoring device of claim 13, wherein the user parameter comprises a device identifier that is specific to the wearable electronic device.

15. The biometric monitoring device of claim 12, wherein the transceiver is configured to communicate with the electronic device via at least one of: Bluetooth, IEEE 802.11 (Wi-Fi), near field communication (NFC), IEEE 802.15.4, ANT+, and ISO 18000-6C.

16. A non-transitory machine readable medium having stored thereon program code that, when executed by one or more processors of a biometric monitoring device comprising a plurality of sensors and processing circuitry, causes the biometric monitoring device to update a user profile of a user, said program code comprising code for:
measuring, via a first sensor of a plurality of sensors of the biometric monitoring device, a weight of a user standing on a platform of the biometric monitoring device;
obtaining, via a transceiver of the biometric monitoring device, a user parameter from an electronic device associated with the user, the user parameter being specific to the user;
comparing the user parameter to a plurality of parameter values respectively associated with a plurality of user profiles stored in a memory of the biometric monitoring device;
comparing the measured weight of the user to a plurality of weight values respectively associated with the plurality of user profiles;
identifying a first user profile of the plurality of user profiles as corresponding to the user based on comparing the user parameter to the plurality of parameter values and comparing the measured weight to the plurality of weight values; and
updating a weight value of the first user profile with the measured weight.

* * * * *